United States Patent [19]
Niigata et al.

[11] Patent Number: 5,453,514
[45] Date of Patent: Sep. 26, 1995

[54] PYRAZOLE DERIVATIVES AND COMPOSITIONS AND METHODS OF USE AS MAILLARD REACTION INHIBITORS

[75] Inventors: Kunihiro Niigata, Saitama; Tatsuya Maruyama, Ibaraki; Hisataka Shikama, Tokyo; Toshiyuki Takasu, Ibaraki; Masako Umeda, Ibaraki; Eiko Hirasaki, Ibaraki; Satoshi Hayashibe, Tokyo; Takenori Kimura, Ibaraki, all of Japan

[73] Assignee: Yamanouchi Pharmaceutical Co., Ltd., Tokyo, Japan

[21] Appl. No.: 178,395

[22] Filed: Dec. 23, 1993

[30] Foreign Application Priority Data

| Dec. 25, 1992 | [JP] | Japan | 4-359138 |
| Mar. 31, 1993 | [JP] | Japan | 5-098745 |
| Apr. 2, 1993 | [JP] | Japan | 5-100330 |
| Apr. 13, 1993 | [JP] | Japan | 5-110956 |
| Apr. 15, 1993 | [JP] | Japan | 5-113665 |

[51] Int. Cl.$^6$ .................. C07D 231/38; C07D 231/54; A61K 31/41; A61K 31/415
[52] U.S. Cl. .................. 548/362.5; 548/370.1
[58] Field of Search .................. 548/362.5, 370.1; 514/406, 405, 383

[56] References Cited

U.S. PATENT DOCUMENTS

| 4,758,583 | 7/1988 | Cerami et al. | 514/399 |
| 4,908,446 | 3/1990 | Ulrich et al. | 514/238.5 |
| 4,983,604 | 1/1991 | Ulrich et al. | 540/553 |
| 5,100,919 | 3/1992 | Ulrich et al. | 514/635 |
| 5,106,877 | 4/1992 | Ulrich et al. | 514/635 |
| 5,114,943 | 5/1992 | Ulrich et al. | 514/256 |
| 5,130,324 | 7/1992 | Ulrich et al. | 514/357 |
| 5,130,337 | 7/1992 | Ulrich et al. | 514/632 |
| 5,175,192 | 12/1992 | Ulrich et al. | 514/614 |
| 5,221,683 | 6/1993 | Ulrich et al. | 514/352 |
| 5,238,963 | 8/1993 | Cerami et al. | 514/632 |
| 5,243,071 | 9/1993 | Ulrich et al. | 562/560 |
| 5,254,593 | 10/1993 | Ulrich et al. | 514/635 |
| 5,334,617 | 8/1994 | Ulrich et al. | 514/562 |

OTHER PUBLICATIONS

Chem. Abstracts vol. 69: #59251k (1968).
Chem. Abstracts, 79: #29768c (1973).
Chem. Abstracts, 87: #196219s (1977).
Bierowska–Charytonowicz et al. Search for new aminoguanidine derivatives with immunosuppressive and cytostatic properties. Arch. Immunol. Ther. Exp. 24: 871, (1976).
De et al. 1936. Synthesis in the pyrazolone series. Part IV. Actions of aminoguanidines on beta–ketonic esters and beta–diketones. J. Indian. Chem. Soc. 13: 509.
Menichi et al. 1984. Conversion of pyrimidines into amidinopyrazole by action of aminoguanidine hydrochloride. Heterocycles, 22: 2013.
Novinson et al. 1974. Synthesis of unsymmetrical 2,4–dialkylpyrazolo[1,5–a]–1,3,5,–triazines. Heterocyclic Chem. 11: 691.
Scott et al. 1952. Studies in the pyrazole series. I. Halogenation of the 1–guanylpyrazoles. J. Am. Chem. Soc. 74: 4562.
Vogel et al. 1975. Neue synthesen von pyrazolo[1,5–a]–s–triazinen. Helv. Chim. Acta. 58: 761.
Zelenin et al. 1987. New data on the reaction of 1,4–bifunctional derivatives of hydrazine. Zh. Obshch. Khim. 57: 584.

*Primary Examiner*—David B. Springer
*Attorney, Agent, or Firm*—Klauber & Jackson

[57] ABSTRACT

A Maillard reaction inhibitor containing, as an active ingredient, an amidinoheterocyclic derivative or its pharmaceutically acceptable salt, which is useful for the prevention and/or cure of various complications of diabetes and maturity-onset disorders. The amidinoheterocyclic derivatives are also useful as Maillard reaction inhibitors for cosmetics, external endermic medicines, foods, drinks, luxury grocery items and functional foods.

36 Claims, No Drawings

PYRAZOLE DERIVATIVES AND COMPOSITIONS AND METHODS OF USE AS MAILLARD REACTION INHIBITORS

FIELD OF THE INVENTION

The present invention relates to pyrazole derivatives and their salts, which have a Maillard reaction inhibiting activity and are useful for prevention and/or cure of various complications of diabetes and maturity-onset disorders.

Recently, denaturation of proteins by glucose has become greatly highlighted as one factor of causing complications of diabetes, which is considered to be caused by the Maillard reaction occurring in living bodies.

A Maillard reaction is considered to be a series of reactions, in which the amino groups of proteins are non-enzymatically saccharified (glycated) with glucose to form Amadori rearrangement products as primary glycation products and the proteins are cross-linked and denatured by the advanced glycation to give advanced glycation end products (AGE) which are brown and are hardly soluble and which are hardly decomposed by proteases.

The advancement of the non-enzymatical glycation or the formation of AGE proteins by the reaction is remarkable especially under hyperglycemic conditions or in the protein sites where the speed of metabolizing proteins is low or proteins are not metabolized. It is considered that the reaction causes denaturation, hypergasia or functional disorder of proteins in various protein sites in diabetics, for example, hemoglobin, serum albumin, collagen and elastin in connective tissues, myelin, lens crystallin of eyeballs, etc. in them, and is one factor of causing complications of diabetes, such as retinopathy, nephropathy, cardiovascular disorders, neuropathy, cataract, etc. In addition, the Maillard reaction in living bodies is considered to be one mechanism of aging and it is presumed that the reaction has a close relation to the maturity-onset disorders.

Therefore, it is considered extremely effective to inhibit the Maillard reaction to inhibit the advancement of the non-enzymatic glycation and the formation of AGE products for various disorders such as various complications of diabetes and various senile disorders. Heretofore, development and study of compounds having a Maillard reaction inhibiting activity has been attempted.

Various compounds having a Maillard reaction inhibiting activity have heretofore been reported.

For instance, mentioned are aminoguanidine, α-hydrazinohistidine, lysine and their mixtures described in Japanese Patent Laid-Open No. 62-142114, which were reported as Maillard reaction inhibitors. It is reported that the described compounds react with the carbonyl moiety in the Amadori rearrangement products of the primary glycation products to block the moiety to thereby inhibiting the secondary glycation, and finally, inhibiting the crosslinking of proteins and the resultant formation of AGE products.

SUMMARY OF THE INVENTION

We, the present inventors, have found that various pyrazole derivatives of the general formula I, which are quite different from conventional Maillard reaction inhibiting compounds in their chemical structures, have excellent effects as Maillard reaction inhibitors. On this basis, we have made the present invention.

Specifically, the present invention provides a method of inhibiting the formation of advanced glycation endproducts which comprises administration of a compound of the general formula I

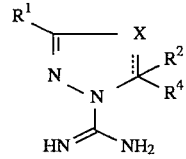

wherein $R^1$ represents a hydrogen atom, a lower alkyl group, or a phenyl group;

$R^2$ represents a hydrogen atom, a lower alkyl group, a phenyl group, an amino group, a lower alkoxy group, a carboxyl group, or a lower alkoxycarbonyl group; X represents a nitrogen atom, or a group of a formula —$CR^3$—; and $R^3$ represents a hydrogen atom, a lower alkyl group, a phenyl group, a halogen atom, or a lower alkanoyl group;

the dotted line represents an optional double bond when X is $CR^3$—

$R^4$ represents a hydroxy group when the optional double bond is not present;

with the proviso that when X represents $CR^3$— and $R^2$ represents hydrogen and the optional double bond is present, then $R^1$ together with $R^3$ can be a —CH=CH—CH=CH— group, optionally substituted by a hydrogen atom, a hydroxyl group, a nitro group, an amino group or a sulfamoyl group;

with the further proviso that when $R^1$ and $R^2$ both represent a lower alkyl group and X represents $CR^3$— and the dotted line represents a double bond then $R^3$ represents:

(i) a fluorine atom, a nitro group, an unsubstituted lower alkyl group having 3 or more carbon substituted by a lower alkanoyl group; or (ii) a lower alkyl group substituted by any of a halogen atom, a lower alkanoyl group, a lower alkoxy group, a lower alkoxycarbonyl group and a phenyl group of the formula:

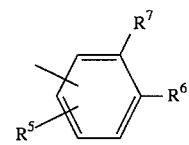

in which $R^5$ and $R^6$ and $R^7$ are the same or different and each represents a hydrogen atom, and amino group, a nitro group, a hydroxyl group, a lower alkyl group, a lower alkoxy group, a lower alkoxycarbonyl group or an aralkyloxy group, and $R^6$ and $R^7$ together may form a lower alkylenedioxy group; or (iii) a carbonyl group substituted by any of a hydroxyl group, a lower alkyl group, an aralkyloxy group, an optionally lower alkyl-substituted amino group and an optionally lower alkoxy substituted lower alkoxy group; or (iv) together with $R^2$ can form a lower alkylene group having 3 or more carbon atoms;

with the still further proviso that when X represents $CR^3$—, $R^3$ represents hydrogen, the double bond is present and $R^2$ represents an amino group, then $R^1$ can represent a lower alkyl-substituted or unsubstituted thienyl or furyl group, a phenyl-substituted lower alkyl or lower alkenyl group, or a phenyl group of the formula in which $R^8$, $R^9$ and $R^{10}$ are the same or different and each represents a hydrogen atom, a halogen atom, an amino group, a nitro group, or an optionally halogen-substituted lower alkyl or lower alkoxy group;

and with the still further proviso that when X represents $CR^3$—, the optional bond is not present and $R^4$ is a hydroxy group, then $R^1$ and R2 are the same or different and each represents a halogen atom-substituted or unsubstituted lower alkyl group; $R^3$ represents a hydrogen atom; and $R^2$ and $R^3$ may together form a lower alkylene group;

and the pharmaceutically acceptable acid addition salts thereof.

Effect of the Invention:

The compounds of formula (I) and their pharmaceutically acceptable salts of the present invention have a Maillard reaction inhibiting activity as well as a low toxicity. Therefore, they are useful for prevention and/or cure of various complications of diabetes, for example, retinopathy, nephropathy, cardiovascular disorders such as coronary cardiopathy, peripheral cardiovascular disorders or cerebrovascular disorders, diabetic neuropathy, cataract, and arteriosclerosis and atherosclerosis which are considered to be caused by the Maillard reaction.

In addition, they are expected to be useful also as medicines for prevention and/or cure of atherosclerosis, senile cataract and cancer which are considered to be caused by aging of proteins.

Moreover, since they may prevent crosslinking of proteins such as collagen and elastin, they may also be used as cosmetics and external endermic medicines.

Further, it is well known that the Maillard reaction has relation to deterioration of proteins and amino acids not only in living bodies but also in foods, drinks and luxury grocery items, the compounds of the present invention may be used as the Maillard reaction inhibitor not only in the functional foods for the above-mentioned medicines and cosmetics but also in foods, drinks and luxury grocery items containing proteins and amino acids.

DETAILED DESCRIPTION OF THE INVENTION

More particularly, the present invention provides a method of inhibiting the formation of advanced glycation endproducts which comprises administration of a compound of the general formula I

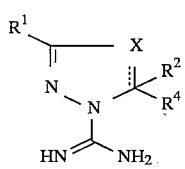

(I)

wherein $R^1$ represents a hydrogen atom, a lower alkyl group, or a phenyl group;

$R^2$ represents a hydrogen atom, a lower alkyl group, a phenyl group, an amino group, a lower alkoxy group, a carboxyl group, or a lower alkoxycarbonyl group; X represents a nitrogen atom, or a group of a formula —$CR^{3-}$; and $R^3$ represents a hydrogen atom, a lower alkyl group, a phenyl group, a halogen atom, or a lower alkanoyl group;

the dotted line represents an optional double bond when X is $CR^3$—

$R^4$ represents a hydroxy group when the optional double bond is not present;

with the proviso that when X represents $CR^3$— and $R^2$ represents hydrogen and the optional double bond is present, then $R^1$ together with $R^3$ can be a —CH=CH—CH=CH— group, optionally substituted by a hydrogen atom, a hydroxyl group, a nitro group, an amino group or a sulfamoyl group;

with the further proviso that when $R^1$ and $R^2$ both represent a lower alkyl group and X represents $CR^3$— and the dotted line represents a double bond then $R^3$ represents:

(i) a fluorine atom, a nitro group, an unsubstituted lower alkyl group having 3 or more carbon substituted by a lower alkanoyl group; or (ii) a lower alkyl group substituted by any of a halogen atom, a lower alkanoyl group, a lower alkoxy group, a lower alkoxycarbonyl group and a phenyl group of the formula:

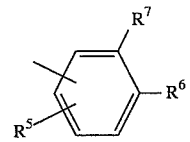

in which $R^5$ and $R^6$ and $R^7$ are the same or different and each represents a hydrogen atom, and amino group, a nitro group, a hydroxyl group, a lower alkyl group, a lower alkoxy group, a lower alkoxycarbonyl group or an aralkyloxy group, and $R^6$ and $R^7$ together may form a lower alkylenedioxy group; or (iii) a carbonyl group substituted by any of a hydroxyl group, a lower alkyl group, an aralkyloxy group, an optionally lower alkyl-substituted amino group and an optionally lower alkoxy substituted lower alkoxy group; or (iv) together with $R^2$ can form a lower alkylene group having 3 or more carbon atoms;

with the still further proviso that when X represents $CR^3$—, $R^3$ represents hydrogen, the double bond is present and $R^2$ represents an amino group, then $R^1$ can represent a lower alkyl-substituted or unsubstituted thienyl or furyl group, a phenyl-substituted lower alkyl or lower alkenyl group, or a phenyl group of the formula

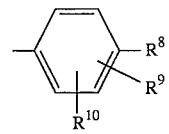

in which $R^8$, $R^9$ and $R^{10}$ are the same or different and each represents a hydrogen atom, a halogen atom, an amino group, a nitro group, or an optionally halogen-substituted lower alkyl or lower alkoxy group;

and with the still further proviso that when X represents $CR^3$—, the optional bond is not present and $R^4$ is a hydroxy group, then $R^1$ and R2 are the same or different and each represents a halogen atom-substituted or unsubstituted lower alkyl group; $R^3$ represents a hydrogen atom; and $R^2$ and $R^3$ may together form a lower alkylene group;

and the pharmaceutically acceptable acid addition salts thereof.

Unless otherwise specifically defined, the terminology "lower" as referred to herein for the definition of the general formula means a linear or branched carbon chain having from 1 to 6 carbon atoms.

The "lower alkyl group" includes, for example, a methyl group, an ethyl group, a propyl group, an isopropyl group, a butyl group, an isobutyl group, a sec-butyl group, a tert-butyl group, a pentyl group, and isopentyl group, a neopentyl group, a tert-pentyl group, a 1-methylbutyl group, a 2-methylbutyl group, a 1,2-dimethylpropyl group, a hexyl group, an isohexyl group, etc.

The "lower alkyl group having 3 or more carbon atoms" is an alkyl group having from 3 to 6 carbon atoms of the above-mentioned lower alkyl groups, which includes, for example, a propyl group, a butyl group, an isobutyl group, a pentyl group and a hexyl group.

The "lower alkanoyl group" includes, for example, a formyl group, acetyl group, a propionyl group, a butyryl group, a isobutyryl group, a valeryl group, an isovaleryl group, a pivaloyl group, a hexanoyl group, etc.

The "lower alkoxycarbonyl group" includes, for example, a methoxycarbonyl group, an ethoxycarbonyl group, a propoxycarbonyl group, an isopropoxycarbonyl group, a butoxycarbonyl group, and isobutoxycarbonyl group, a sec-butoxycarbonyl group, a tert-butoxycarbonyl group, a pentyl(amyl)oxycarbonyl group, an isopentyl(amyl)oxycarbonyl group, a hexyloxycarbonyl group, an isohexyloxycarbonyl group, etc.

The "lower alkoxy group" includes, for example, a methoxy group, an ethoxy group, a propoxy group, an isopropoxy group, a butoxy group, an isobutoxy group, a sec-butoxy group, a tert-butoxy group, a pentyloxy (amyloxy) group, an isopentyloxy group, a tert-pentyloxy group, a neopentyloxy group, a 2-methylpropoxy group, a 1,2-dimethylpropoxy group, a 1-ethylpropoxy group, a hexyloxy group, etc.

The "aralkyloxy group" is preferably a phenyl-lower alkoxy group, including, for example, a benzyloxy group, a phenethyloxy group, a phenylpropoxy group, a phenylbutoxy group, a phenylpentyloxy group, a phenylhexyloxy group, etc. Preferred is a benzyloxy group.

The "lower alkylenedioxy group" is a group having oxo groups at the both ends of a lower alkylene chain, which includes, for example, a methylenedioxy group (—OCH$_2$O—), an ethylenedioxy group (—O(CH$_2$)$_2$O—), a propylenedioxy group, etc.

The "lower alkenyl group" is an alkenyl group having from 2 to 6 carbon atoms, including, for example, a vinyl group, an allyl group, a 1-propenyl group, a butenyl group, a pentenyl group, a hexenyl group, etc.

The "lower alkylene group" includes, for example, a methylene group, an ethylene group, a propylene group, a butylene group, a pentamethylene group, a hexamethylene group, etc.

The "lower alkylene group having 3 or more carbon atoms" is preferably an alkylene group having from 3 to 6 carbon atoms, including, for example, a propylene group, a tetramethylene group, a 1-methyltrimethylene group, a 2-methyltrimethylene group, a 3-methyltrimethylene group, an ethylethylene group, a dimethylethylene group, a pentamethylene group, a methyltetramethylene group, a dimethyltrimethylene groups, a pentamethylene group, a hexamethylene group, etc. Preferred are a propylene group, a tetramethylene group and a pentamethylene group.

The "halogen atom" is preferably a fluorine atom, a chlorine atom, a bromine atom, etc.

The "amino group optionally substituted by a lower alkanoyl group or a lower alkoxycarbonyl group" means an unsubstituted amino group and an amino group substituted by one substituent of the above-mentioned lower alkanoyl group or lower alkoxycarbonyl group. The latter includes, for example, an acetylamino group, a propionylamino group, a butyrylamino group, a methoxycarbonylamino group, an ethoxycarbonylamino group, a propoxycarbonylamino group, etc.

The "halogen atom" is preferably a fluorine atom, a chlorine atom, a bromine atom, etc.

The "lower alkyl group" moiety of the substituted lower alkyl group is preferably a methyl group, an ethyl group or a propyl group. The substituent of the group is as mentioned above. Concretely, the substituent "lower alkanoyl group" is preferably an acetyl group or a propionyl group; the "lower alkoxy group" is preferably a methoxy group or an ethoxy group; and the "lower alkoxycarbonyl group" is preferably a methoxycarbonyl group or an ethoxycarbonyl group.

The "lower alkyl group" of $R^5$, $R^6$ and $R^7$ in the phenyl group of a formula:

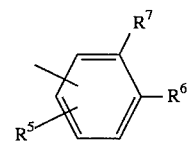

is as mentioned above, and it is preferably a methyl group, an ethyl group or a tert-butyl group.

The "optionally lower alkyl-substituted amino group" of the substituent of the substituted carbonyl group means an unsubstituted amino group or an amino group substituted by one of the above-mentioned alkyl groups. The latter includes, for example, a methylamino group, an ethylamino group, a propylamino group, a butylamino group and a pentylamino group.

The "optionally lower alkoxy-substituted lower alkoxy group" means the above-mentioned lower alkoxy group or a lower alkoxy group substituted by an alkoxy group at any position thereof. The latter is preferably a methoxyethoxy group or an ethoxyethoxy group.

The "lower alkyl-substituted thienyl or furyl group" is a thienyl or furyl group substituted by one of the above-mentioned alkyl groups. It includes, for example, a 2-methylthienyl group, a 2-ethylthienyl group, a 2-propylthienyl group, a 2-methylfuryl group, a 2-ethylfuryl group, a 2-propylfuryl group, etc.

The "halogen-substituted lower alkyl or lower alkoxy group" is the above-mentioned lower alkyl or lower alkoxy group substituted by the above-mentioned halogen atom(s), including, for example, a monochloromethyl group, a monofluoromethyl group, a trifluoromethyl group, a trifluoroethyl group, a monochloromethoxy group, a monofluoromethoxy group, a trifluoromethoxy group, etc.

Equivalent to the compounds of formula (I) for the purposes of the present invention are the pharmaceutically acceptable salts formed with acids. These acid addition salts include, for example, the acid-addition salts with mineral acids such as hydrochloric acid, hydrobromic acid, hydroiodic acid, sulfuric acid, nitric acid, phosphoric acid, etc.; and the acid-addition salts with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid, etc.

A compound of formula (I) may contain an asymmetric carbon atom, depending upon the kind of the substituents.

The present invention also includes medicines containing, as the active ingredient, an isolated optical isomer of a compound of formula (I) or a mixture of optical isomers thereof.

A compound of formula (I) may be isolated as its hydrate or solvate, for example, with ethanol or the like or as its polymorphic substance. The present invention also includes them.

Certain of the compounds of formula I which are active ingredients of the medicines to be provided by the present invention are disclosed in *Chem. Abs.*, 69:59251k; *J. Am. Chem. Soc.*, 74:4562 (1952); *Chem. Abs.*, 79:29768c; *Chem. Abs.*, 87:196219s; *Helv. Chim. Acta*, 58:761 (9175); *J. Heterocyclic. Chem.*, 11:691 (1974); Japanese Patent Laid-Open No. 50-151872; *Arch. Immunol. Ther. Exp.*, 24:871 (1976); *Heterocycles*, 22:2013 (1984); *Zh. Obshch. Khim.*, 57:584 (1987); and *J. Indian. Chem. Soc.*, 13:509 (1936); and almost all of them are known.

However, these publications do not disclose that these amidinoheterocyclic derivatives possess Maillard reaction inhibiting activity.

In one embodiment, the present invention comprises a Maillard reaction inhibitor containing, as an active ingredient, an amidinoheterocyclic derivative of the following general formula (Ia) or its pharmaceutically acceptable salt, and the object of the present invention is to provide the inhibitor of the formula:

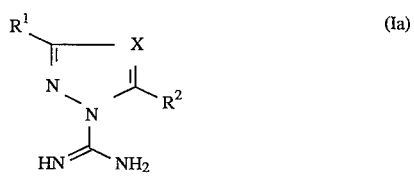

wherein $R^1$ represents a hydrogen atom, a lower alkyl group, or phenyl group;

$R^2$ represents a hydrogen atom, a lower alkyl group, a phenyl group, an amino group, a lower alkoxy group, a carboxyl group, or a lower alkoxycarbonyl group; X represents a nitrogen atom, or a group of a formula —$CR^3$=;

and $R^3$ represents a hydrogen atom, a lower alkyl group, a phenyl group, a halogen atom, or a lower alkanoyl group.

Representative compounds of formula Ia include:

(1) 1-Amidino-1,2,4-triazole and its pharmaceutically acceptable salts;
(2) 1-Amidinopyrazole and its pharmaceutically acceptable salts;
(3) 1-Amidino-3,5-dimethylpyrazole and its pharmaceutically acceptable salts;
(4) 1-Amidino-4-chloro-3,5-dimethylpyrazole and its pharmaceutically acceptable salts;
(5) 1-Amidino-4-bromo-3,5-dimethylpyrazole and its pharmaceutically acceptable salts;
(6) 1-Amidino-3,5-dimethyl-4-phenylpyrazole and its pharmaceutically acceptable salts;
(7) 1-Amidino-5-aminopyrazole and its pharmaceutically acceptable salts;
(8) 1-Amidino-5-amino-3-methylpyrazole and its pharmaceutically acceptable salts;
(9) 1-Amidino-5-amino-3-phenylpyrazole and its pharmaceutically acceptable salts;
(10) 1-Amidino-5-methoxy-3-methylpyrazole and its pharmaceutically acceptable salts;
(11) 1-Amidino-5-ethoxy-3-methylpyrazole and its pharmaceutically acceptable salts;
(12) (1-Amidino-3-methylpyrazol-5-yl)carboxylic acid and its pharmaceutically acceptable salts;
(13) Ethyl (1-amidino-3-methylpyrazol-5-yl)carboxylate and its pharmaceutically acceptable salts;
(14) 4-Acetyl-1-amidino-5-methylpyrazole and its pharmaceutically acceptable salts;
(15) 1-Amidino-3,5-diphenylpyrazole and its pharmaceutically acceptable salts;
(16) 1-Amidino-3,4,5-trimethylpyrazole and its pharmaceutically acceptable salts; and
(17) 1-Amidino-3,5-dimethyl-4-ethylpyrazole and its pharmaceutically acceptable salts.

Of these, preferred compounds are Compounds (2), (3), (4), (5), (7), (8), (9), (13) and (14); and especially preferred is compound (3).

Preparation of the compounds of formula (Ia):

Most of the amidinoheterocyclic derivatives (Ia) and their salts of the present invention are produced in accordance with the methods described in the above-mentioned publications. Of the compounds of formula (Ia) which are the active ingredients of the present invention, those not specifically described in the above-mentioned publications may also be produced in accordance with the methods described in the above-mentioned publications or by their modifications.

In a second embodiment, the present invention comprises the novel amidinoindazole derivatives of formula Ib, and their preparation constitutes a further aspect of the present invention.

These novel amidinoindazole derivatives and their salts are those of the general formula Ib

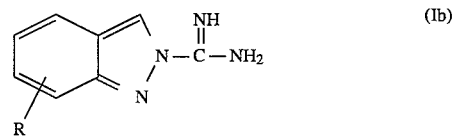

wherein R represents a hydrogen atom, a hydroxyl group, a nitro group, an amino group or a sulfamoyl group.

As mentioned above, R in the compounds of Formula (Ib) of the present invention represents a hydrogen atom, a hydroxyl group, a nitro group, an amino group or a sulfamoyl group.

R may be bonded to any carbon atom on the benzene ring of the indazole moiety of the compounds of the present invention.

The compounds of Formula (Ib) of the present invention form salts with acids.

The compounds of formula Ib of the present invention may be produced by various methods. Some typical methods for producing the compounds of formula Ib are mentioned below:

First Method:

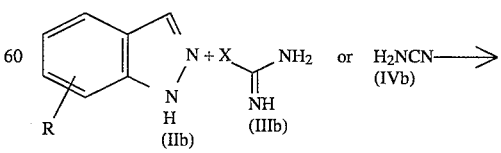

-continued
First Method:

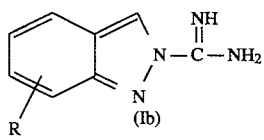
(Ib)

wherein R is as above; and X represents a halogen atom.

The halogen atom of X includes, for example, a chlorine atom, a bromine atom, etc.

The compounds of formula Ib of the present invention may be produced by reacting an indazole compound of formula IIb and a halogenoformamidine of formula IIIb or its salt or the cyanamide of formula IVb for N-amidination.

The reaction is effected by warming or heating under reflux the indazole compound of formula IIb and a reaction-corresponding amount of the halogenoformamidine IIIb or its salt or the cyanamide of formula IVb in an inert solvent.

The inert solvent usable in the reaction includes, for example, benzene, tetrahydrofuran (THF), chloroform, ethyl acetate, toluene, 1,4-dioxane, etc.

Where a halogenoformamidine is used alone in the reaction, addition of an acid such as hydrochloric acid, hydrobromic acid or nitric acid to the reaction system is preferred.

Second Method:

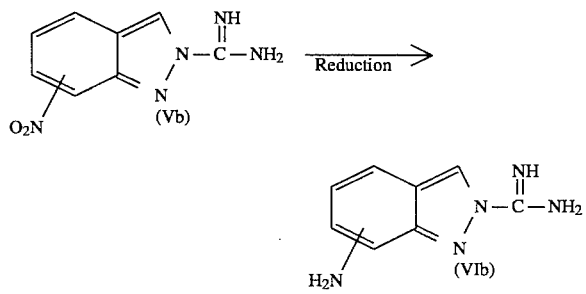

Compounds (IVb) of the present invention may be produced by reducing the nitro compound of formula (Vb).

The reduction may be effected by an ordinary process, for example, in the presence of a noble metal catalyst such as palladium carbon, platinum oxide or the like for catalytic reduction, in a solvent which is generally used in catalytic reduction such as methanol, ethanol, ethyl acetate or the like, under normal pressure or elevated pressure.

In a third embodiment, the present invention comprises the novel pyrazole derivatives of formula Ic, and their preparation constitutes a further aspect of the present invention.

These novel pyrazole derivatives are those of the general formula (Ic) and their salts are those of the formula

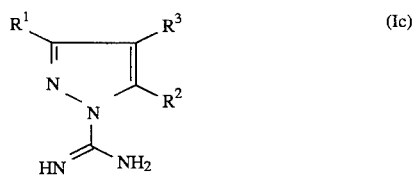

wherein
$R^1$ represents a lower alkyl group;
$R^2$ represents (i) a fluorine atom, a nitro group, an unsubstituted low alkyl having 3 or more carbon atoms, or an amino group optionally substituted by a lower alkanoyl group or a lower alkoxycarbonyl group; or (ii) a lower alkyl group substituted by any of a halogen atom, a lower alkanoyl group, a lower alkoxy group, a lower alkoxycarbonyl group and a phenyl group of a formula:

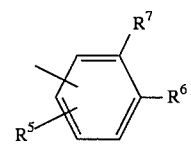

in which
$R^6$, $R^7$ and $R^8$ are same or different and each represents a hydrogen atom, an amino group, a nitro group, a hydroxyl group, a lower alkyl group, a lower alkoxy group, a lower alkoxycarbonyl group or an aralkyloxy group, and $R^6$ and $R^7$ may together form a lower alkylenedioxy group; or (iii) a carbonyl group substituted by any of a hydroxyl group, a lower alkyl group, an aralkyloxy group, an optionally lower alkyl-substituted amino group and an optionally lower alkoxy-substituted lower alkoxy group; and $R^2$ and $R^3$ may together form a lower alkylene group having 3 or more carbon atoms.

Some typical methods for producing the compounds of formula Ic are mentioned below.

First Method:

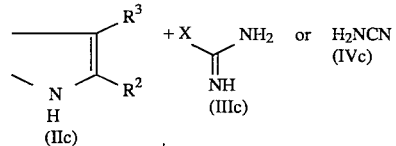

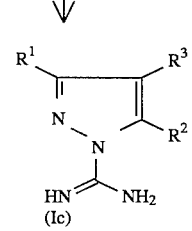

where $R^1$, $R^2$ and $R^3$ have the same definitions as mentioned above for formula Ic; and X represents a halogen atom.

The halogen atom of X includes, for example, a chlorine atom, a bromine atom, etc.

The compounds of formula Ic of the present invention may be produced by reacting a pyrazole compound of formula IIc and a halogenoformamidine salt of formula IIIc or cyanamide of formula IVc for N-amidination.

The reaction is effected by warming or heating under reflux the pyrazole compound of formula IIc and a reaction-corresponding amount of the halogenoformamidine salt (IIIc) or cyanamide (IVc) in a solvent.

The solvent usable in the reaction includes, for example, benzene, tetrahydrofuran (THF), chloroform, ethyl acetate, toluene, 1,4-dioxane, etc.

Where cyanamide is used in the reaction, the pyrazole compound (IIc) to be reacted therewith is preferably in the form of its acid-additional salt with hydrochloric acid, hydrobromic acid, nitric acid or the like.

Second Method:

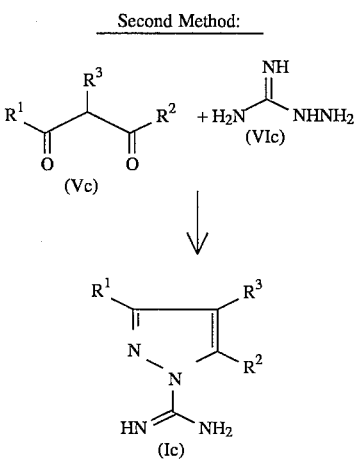

where $R^1$, $R_2$ and $R^3$ have the same definitions as mentioned above for formula Ic.

The compounds of formula (Ic) of the present invention may be produced by reacting the diketone compounds of formula (Vc) and an aminoguanidine salt of formula (VIc) for cyclization.

The diketone compound (Vc) is reacted with a reaction-corresponding amount of the aminoguanidine salt (VIc) in a solvent at room temperature or under heat.

The solvent usable in the reaction includes, for example, water, methanol, ethanol, tetrahydrofuran (THF), 1,4-dioxane, etc.

The acid-addition salt of aminoguanidine includes its hydrochloride, hydrobromide and nitrate.

Third Method (nitration):

Of the compounds of formula (Ic) of the present invention, those where $R^3$ is a nitro group may be produced by ordinary nitration.

For instance, compound of formula (Ic) of the present invention where $R^3$ is a hydrogen atom and a reaction-corresponding amount or excess amount of a nitrating reagent are stirred in an inert solvent with cooling with ice or at room temperature to obtain the corresponding compound of formula (Ic) where $R^3$ is a nitro group. As the inert solvent, preferred are acetonitrile, acetic acid and the like.

Fourth Reaction (reduction):

Of the compounds of formula (Ic) of the present invention, those where $R^3$ is an amino group may be produced by reducing compound (Ic) where $R^3$ is a nitro group.

The reduction may be effected by an ordinary process. For instance, for catalytic reduction, compound (Ic) where $R^3$ is a nitro group is reduced in the presence of a noble metal catalyst such as palladium-carbon, platinum oxide or the like, in a solvent which is generally used in catalytic reduction, such as methanol, ethanol, ethyl acetate or the like, at normal pressure or elevated pressure.

Fifth Method:

Of the compounds of formula (Ic) of the present invention, those where $R^3$ is a carboxylic acid group may be produced by removing the benzyl group from the corresponding benzyl ester.

The removal of the benzyl group may be effected in accordance with the above-mentioned fourth method. For instance, the benzyl group may easily be removed by hydrogenation of the corresponding benzyl ester in the presence of a noble metal catalyst such as palladium-carbon, platinum oxide or the like, in methanol, ethanol, ethyl acetate or the like ordinary solvent.

In a fourth embodiment, the present invention comprises the novel 5-aminopyrazole derivatives of formula Id, and their preparation constitutes a further aspect of the present invention.

These novel 5-aminopyrazole derivatives and their salts are those of the general formula Id

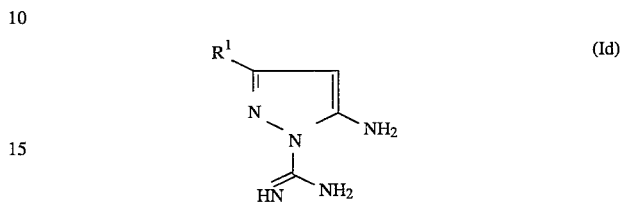

where $R^1$ represents a lower alkyl group having 3 or more carbon atoms, a lower alkyl-substituted or unsubstituted thienyl or furyl group, a phenyl-substituted lower alkyl or lower alkenyl group, or a phenyl group of a formula:

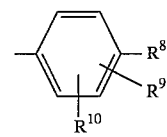

in which $R^8$, $R^9$ and $R^{10}$ are same or different and each represents a hydrogen atom, a halogen atom, an amino group, a nitro group, or an optionally halogen-substituted lower alkyl or lower alkoxy group;

provided that when $R^8$ is a hydrogen atom or a bromine atom, one of $R^9$ and $R^{10}$ is a group except hydrogen.

Methods of producing compounds of formula (Id):

The compounds of the present invention may be produced by various methods. Some typical methods for producing the compounds of formula (Id) are mentioned below.

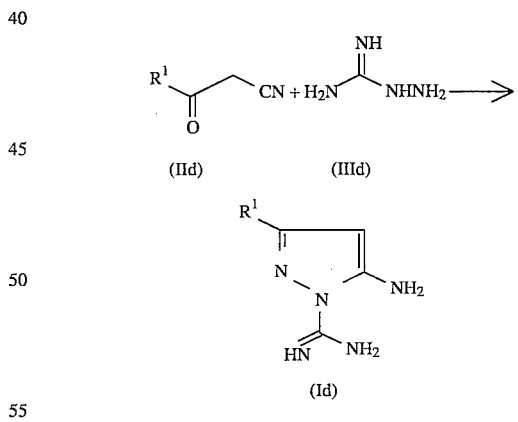

where $R^1$ has the same definition as mentioned above for formula Id.

Compounds (Id) of the present invention may be produced by reacting an acetonitrile compound of Formula (IId) and an aminoguanidine salt of Formula (IIId) for cyclization.

The cyclization is conducted by heating optionally under reflux the acetonitrile compound (IId) and a reaction-corresponding amount of the aminoguanidine salt (IIId) in a solvent.

The solvent usable in the reaction includes, for example, methanol, ethanol, THF, DMF, acetic acid, etc.

As acid-addition salts of aminoguanidine, mentioned are its hydrochloride, hydrobromide, nitrate, etc.

Second Method (reduction):

Of the compounds of formula (Id) of the present invention, those where $R^1$ is a phenyl-substituted lower alkyl group or any of $R^8$, $R^9$ and $R^{10}$ is an amino group may be produced by reducing Compound (I) where $R^1$ is a phenyl-substituted lower alkenyl group or any of $R^2$, $R^3$ and $R^4$ is a nitro group.

The reduction may be effected by an ordinary process. For instance, for obtaining the Compound of formula (If) where $R^1$ is a phenyl-substituted lower alkyl group by catalytic reduction, the Compound of Formula (If) where $R^1$ is a phenyl substituted lower alkenyl group is reduced in the presence of a noble metal catalyst such as palladium-carbon, platinum oxide or the like, in a solvent which is generally used in catalytic reduction, such as methanol, ethanol, ethyl acetate or the like, at normal pressure or elevated pressure. For obtaining Compound (Id) where any of $R^8$, $R^9$ and $R^{10}$ is an amino group, Compound (Id) where any of $R^8$, $R^9$ and $R^{10}$ is a nitro group is reduced with a metal such as iron, zinc, tin or the like in the presence of hydrochloric acid, acetic acid, ammonium chloride or the like in a solvent such as water, acetic acid or the like, at room temperature or under heat.

In a fifth embodiment, the present invention comprises the novel 5-hydroxypyrazoline derivatives of formula Ie, and their preparation constitutes a further aspect of the present invention.

These novel 5-hydroxypyrazoline derivatives and their salts are those of the general formula Ie

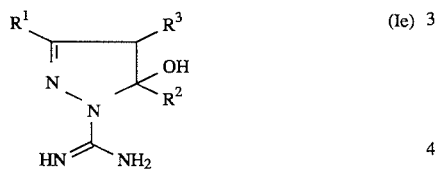

where $R^1$ and $R^2$ are same or different and each represents a halogen atom-substituted or unsubstituted lower alkyl group, provided that when one of them is methyl group, the other is a group except it;

$R^3$ represents a hydrogen atom; and $R^2$ and $R^3$ may together form a lower alkylene group.

Methods of producing the formula of Compounds (Ie):

The compounds of the present invention may be produced by various methods. One typical method for producing Compounds (Ie) is mentioned below.

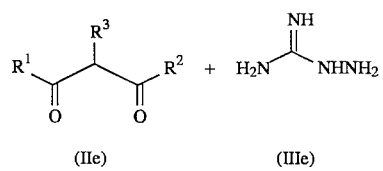

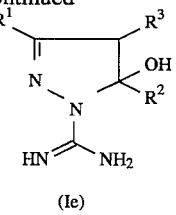

where $R^1$, $R^2$ and $R^3$ have the same definitions as mentioned above for formula Ie.

compounds (Ie) of the present invention may be produced by reacting the diketone compound of Formula (IIe) and amidinoguanidine (IIIe) or its salt for cyclization.

The cyclization is effected by stirring the diketone compound (IIe) and a reaction-corresponding amount of amidinoguanidine (IIIe) or its salt in an inert solvent at room temperature or under heat.

The inert solvent usable in the reaction includes, for example, water, methanol, ethanol, THF, DMF, etc.

Pharmaceutical Effect of the Compounds of formula (I):

The Maillard reaction inhibiting activity of the compounds of the present invention has been verified by the following test method, and the compounds have an excellent effect.

Maillard reaction inhibiting activity test:

Test method:

Lysozyme and ribose were dissolved in 0.1M sodium phosphate buffer (pH 7.4) containing 3 mM of sodium azide to have a concentration of 6 mg/ml and 100 mM, respectively, and incubated for 7 days at 37° C. After the incubation, a certain amount of it was taken out and subjected to electrophoresis with SDS-PAGE. After the electrophoresis, this was stained with 0.04% Coomassie Brilliant Blue R-250 and the amounts of the dimer and trimer formed were determined with a densitometer.

The compound of the present invention to be tested was added prior to the incubation in a concentration of 1 mM, 3 mM, 10 mM or 30 mM. The inhibiting effect of the compound of each concentration to the dimer and trimer was measured, and the $IC_{50}$ value of the compound was obtained from the measured data.

The Maillard reaction inhibiting activity of compounds of formula (Ia) of the present invention as obtained by the above-mentioned test is shown in Table 1 below along with the substituents of them.

TABLE 1

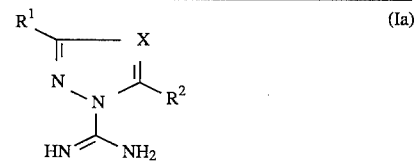

| Test No. | $R^1$ | $R^2$ | X | $R^3$ | Salt | Inhibiting Activity ($IC_{50}$, mM) |
|---|---|---|---|---|---|---|
| 1 | H | H | N | — | HCl | 27.1 |
| 2 | H | H | $CR^3$ | H | HCl | 8.8 |
| 3 | Me | Me | $CR^3$ | H | HCl | 7.7 |
| 4 | Me | Me | $CR^3$ | Cl | $HNO_3$ | 10.4 |
| 5 | Me | Me | $CR^3$ | Br | $HNO_3$ | 9.3 |
| 6 | Me | Me | $CR^3$ | Ph | HCl | 12.3 |
| 7 | H | $NH_2$ | $CR^3$ | H | HCl | 4.3 |
| 8 | Me | $NH_2$ | $CR^3$ | H | HCl | 4.7 |

TABLE 1-continued $$\underset{HN}{\overset{R^1}{\underset{N}{\|}}}\underset{NH_2}{\overset{X}{\underset{N}{\|}}}\overset{\|}{\underset{R^2}{\|}} \quad (Ia)$$

| Test No. | $R^1$ | $R^2$ | X | $R^3$ | Salt | Inhibiting Activity ($IC_{50}$, mM) |
|---|---|---|---|---|---|---|
| 9 | Ph | $NH_2$ | $CR^3$ | H | HCl | 2.4 |
| 10 | Me | OMe | $CR^3$ | H | HCl | 27.0 |
| 11 | Me | OEt | $CR^3$ | H | HCl | 26.0 |
| 12 | Me | $CO_2H$ | $CR^3$ | H | HCl | 16.1 |
| 13 | Me | $CO_2Et$ | $CR^3$ | H | HCl | 6.6 |
| 14 | H | Me | $CR^3$ | Ac | HCl | 7.3 |
| 15 | Ph | Ph | $CR^3$ | H | HCl | 30.0 |
| 16 | Me | Me | $CR^3$ | Me | HCl | 27.1 |
| 17 | Me | Me | $CR^3$ | Et | HCl | 26.4 |

Formulation of Medicines:

A medicinal composition containing, as the active ingredient, one or more of the compounds of formula (I), their pharmaceutically acceptable salts, their pharmaceutically acceptable hydrates and the like is formed into tablets, powder, fine granules, granules, capsules, pills, oral liquid, injection, suppositories, ointment, plaster and the like, along with conventional pharmaceutical carriers, vehicles and other additives. They are administered perorally or parenterally.

The clinical dose of the compound of the present invention to patients is suitably determined in consideration of the condition, body weight, age and sex of the patient to which it is given. In general, its peroral dose for an adult is from 0.1 to 500 mg/day, preferably from 10 to 200 mg/day, which is administered all at a time or is divided into plural administrations. Since the dose may vary under various conditions, a smaller dose than the defined range may often be sufficient.

The solid composition of the present invention for peroral administration may be in the form of tablets, powder, granules, etc. In preparing the solid composition of the kind, one or more active substances are blended with at least one inactive diluent such as lactose, mannitol, glucose, hydroxypropyl cellulose, fine crystalline cellulose, starch, polyvinyl pyrrolidone, magnesium metasilicate aluminate, etc. The composition may contain, as usual, any other additives than the inert diluent, for example, a lubricant such as magnesium stearate, a disintegrator such as potassium cellulose glycolate, a stabilizer such as lactose, and a dissolution aid such as glutamic acid or aspartic acid. The tablets and pills may be coated, if desired, with a film of a gastric-soluble or enteric-soluble substance such as sucrose, gelatin, hydroxypropyl cellulose, hydroxypropylmethyl cellulose phthalate or the like.

The peroral liquid composition of the present invention contains a pharmaceutically acceptable emulsifier, solution, suspension, syrup, elixir or the like and contains an ordinary inactive diluent such as pure water or ethanol. The composition may contain, in addition to the inactive diluent, other auxiliaries such as a solubilizer, a dissolution aid, a moisturizer or a suspension, as well as a sweetener, a flavoring, an aromatic and an antiseptic.

The injection for parenteral administration of the present invention contains a germ-free aqueous or non-aqueous solution, suspension or emulsion. The aqueous solution and suspension include, for example, a distilled water for injection and a physiological saline solution. The non-aqueous solution and suspension include, for example, propylene glycol, polyethylene glycol, vegetable oils such as olive oil, alcohols such as ethanol, Polysorbate 80 (trade name), etc. The composition may further contain other additives such as an isotonic agent, an antiseptic, a moisturizer, an emulsifier, a dispersing agent, a stabilizer (for example, lactose), a solubilizer and a dissolution aid. The additives are sterilized, for example, by filtration of them through a bacteria-retentive filter, or by adding a microbicide thereto or by irradiation to them. As the case may be, a germ-free solid composition for injection is prepared and this may be dissolved in a germ-free water or a germ-free solvent for injection before use.

When cosmetics or external endermic medicines containing the Maillard reaction inhibiting compound of the present invention are prepared, they may contain compound (I) or its salt of the present invention in an amount of from 0.05 to 10 parts by weight to the total weight. The cosmetics and external endermic medicines may be prepared by ordinary methods using general cosmetic bases and external medicinal bases.

Foods, drinks, luxury grocery items and functional foods containing the Maillard reaction inhibiting compound of the present invention may also be prepared by ordinary methods.

EXAMPLES

The present invention will be explained in more detail by means of the following examples, Needless to say, the present invention is not limited to only them.

The chemical structural formulae of the compounds of the present invention as obtained in the following examples are shown in the following tables.

Formulation Example

Peroral tablets (film-coated tablets):

| Composition | |
|---|---|
| Core Tablet | |
| Active ingredient of formula (I) | 30 mg |
| Calcium hydrogen phosphate anhydride | 68 mg |
| Crystalline cellulose | 20 mg |
| Light silicic acid anhydride | 2 mg |
| Hydroxypropyl cellulose | 5 mg |
| Calcium Carboxymethyl cellulose | 4.2 mg |
| Magnesium stearate | 0.8 mg |
| Sub-total | 130 mg |
| Coating | |
| Hydroxypropylmethyl cellulose 2910 | 3.8 mg |
| Polyethylene glycol 6000 | 0.5 mg |
| Titanium oxide | 2.0 mg |
| Iron sesquioxide | 0.1 mg |
| Talc | 0.1 mg |
| Sub-total | 6.5 mg |
| Total | 136.5 mg |

130 mg-tablets containing the active ingredient of formula (I) or its pharmaceutically acceptable salt of the invention:

150 g of the active ingredient of formula (I) or its pharmaceutically acceptable salt of the invention, 340 g of calcium hydrogen phosphate anhydride, 100 g of crystalline cellulose and 10 g of light silicic acid anhydride were weighed and put in a fluidized-bed granulation coater (manufactured by Ohkawara Seisakusho KK) and uniformly blended therein. 250 g of 10% hydroxypropyl cellulose solution was sprayed thereover for granulation. After drying, the granules were passed through a 20-mesh sieve, to which added were 21 g of calcium carboxymethyl cellulose and 4 g of magnesium stearate. The resulting granules were tableted in a rotary tableting machine (manufactured by Hata Seisakusho KK), using a pounder of 7 mm×8.4 R, to form tablets of 130 mg/tablet.

The tablets were coated in a coating machine (Freund Industry Co.), where 325 g of a coating liquid comprising 19 g of hydroxypropylmethyl cellulose, 2.5 g of polyethylene glycol 6000, 10 g of titanium oxide, 0.5 g of iron sesquioxide and 0.5 g of talc were sprayed over the tablets. Thus, film-coated tablets each having a coating of 6.5 mg/tablet were obtained.

The preparation of the compounds of the present invention will be explained in more detail by means of the following examples. Needless to say, the present invention is not limited to only them.

The chemical structural formulae of the compounds of the present invention as obtained in the following examples are shown in the following tables.

Example 1

940 mg of indazole and 920 mg of chloroformamidine hydrochloride were heated under reflux in 30 ml of benzene of THF for 5 hours, and the crystals formed were removed by filtration. These were recrystallized from ethanol ether to obtain 826 mg of 2H-indazole-2-carboxamidine hydrochloride.

Physico-chemical properties:
Melting point: 186° to 187° C.

| Elementary analysis (as $C_8H_9N_4Cl$): | | | | |
|---|---|---|---|---|
| | C (%) | H (%) | N (%) | Cl (%) |
| Theoretical | 48.87 | 4.61 | 28.49 | 18.03 |
| Measured | 48.59 | 4.65 | 28.57 | 18.24 |

Mass spectrum (m/z): 160 [(M-HCl)$^+$]

Nuclear magnetic resonance spectrum (DMSO-$d_6$·TMS internal standard): δ: 7.22 (1H, dd, J=8.5, 7.0 Hz), 7.48 (1H, dd, J=9.0, 7.0 Hz), 7.71 (1H, d, J=9 Hz), 7.84 (1H, d, J=8.5 Hz), 9.47 (1H,s), 10.04 (4H, brs)

In the same manner as in Example 1, compounds of the following Examples 2–7 were obtained.

Example 2

End product: 5-Nitro-2H-indazole-2-carboxamidine hydrochloride
Starting compound: 5-Nitroindazole
Physico-chemical properties:
Melting point: 193° to 196° C.

| Elementary analysis (as $C_8H_8N_5O_2Cl$): | | | | |
|---|---|---|---|---|
| | C (%) | H (%) | N (%) | C % |
| Theoretical | 39.77 | 3.34 | 28.98 | 14.67 |
| Measured | 39.45 | 3.32 | 29.25 | 14.86 |

Mass spectrum (m/z): 205 [(M-HCl)$^+$]

Nuclear magnetic resonance spectrum (DMSO-$d_6$·TMS internal standard): δ: 7.87–8.23 (2H, m), 9.06–9.09 (1H, s), 10.26 (4H, brs)

Example 3

End product: 6-Nitro-2H-indazole-2-carboxamidine hydrochloride
Starting Compound: 6-Nitroindazole
Physico-chemical properties:
Melting point: 173° to 175° C.

| Elementary analysis (as $C_8H_8N_5O_2Cl.0.3H_2O$): | | | | |
|---|---|---|---|---|
| | C (%) | H (%) | N (%) | Cl (%) |
| Theoretical | 38.90 | 3.51 | 28.35 | 14.35 |
| Measured | 39.01 | 3.56 | 28.24 | 14.17 |

Mass spectrum (m/z): 205 [(M-HCl)$^+$]

Nuclear magnetic resonance spectrum (DMSO-$d_6$·TMS internal standard): δ: 7.90 (1H, d, J=9.5 Hz), 8.19 (1H, d, J=9.5 Hz), 8.67 (1H, s), 9.66 (1H, s), 10.30 (4H, brs)

Example 4

End product: 7-Nitro-2H-indazole-2-carboxamidine hydrochloride
Starting compound: 7-Nitroindazole
Physico-chemical properties:
Melting point: 230° to 233° C.

| Elementary analysis (as $C_8H_8N_5O_2Cl$): | | | | |
|---|---|---|---|---|
| | C (%) | H (%) | N (%) | Cl (%) |
| Theoretical | 39.77 | 3.34 | 28.98 | 14.67 |
| Measured | 39.67 | 3.22 | 28.98 | 14.56 |

Mass spectrum (m/z): 205 [(M-HCl)$^+$]

Nuclear magnetic resonance spectrum (DMSO-$d_6$·TMS internal standard): δ: 7.35–7.54 (1H, m), 8.38–8.59 (2H, m), 9.76 (1, s), 10.21 (4H, brs)

Example 5

End product: 5-Hydroxy-2H-indazole-2-carboxamidine hydrochloride
Starting compound: 5-Hydroxyindazole
Physico-chemical properties:
Melting point: 188° to 191° C.

| Elementary analysis (as $C_8H_9N_4OCl.1H_2O$): | | | | |
|---|---|---|---|---|
| | C (%) | H (%) | N (%) | Cl (%) |
| Theoretical | 41.34 | 4.86 | 24.10 | 15.25 |
| Measured | 41.21 | 4.74 | 24.22 | 15.31 |

Mass spectrum (m/z): 176 [(M-HCl)$^+$]

Nuclear magnetic resonance spectrum (DMSO-$d_6$·TMS internal standard): δ: 6.87 (1H, d, J=2 Hz), 7.14 (1H, dd, J=2, 9.5 Hz), 7.59(1H, d, J=9.5 Hz), 9.08 (1H, d, J=1 Hz), 9.86 (5H, brs)

Example 6

End product: 6-Hydroxy-2H-indazole-2-carboxamidine hydrochloride
Starting compound: 6-Hydroxyindazole
Physico-chemical properties:
Melting point: 187° to 188° C.

| Elementary analysis (as $C_8H_9N_4OCl.3H_2O$) | | | | |
|---|---|---|---|---|
| | C (%) | H (%) | N (%) | Cl (%) |
| Theoretical | 40.71 | 4.95 | 23.73 | 15.02 |
| Measured | 40.57 | 4.65 | 23.98 | 14.61 |

Mass spectrum (m/z): 176 [(M-HCl)$^+$]

Nuclear magnetic resonance spectrum (DMSO-$d_6$.TMS internal standard): δ: 6.83 (1H, s), 6.90 (1H, d, J=9.1 Hz), 7.69 (1H, d, J=9.1 Hz), 9.32 (1H, s), 9.82 (4H, br), 10.43 (1H, br)

Example 7

End product: 7-Sulfamoyl-2H-indazole-2-carboxamidine hydrochloride
Starting compound: 7-Sulfamoylindazole
Physico-chemical properties:
Melting point: 208° to 209° C.

| Elementary analysis (as $C_8H_{10}N_4O_2SCl.2H_2O$): | | | | | |
|---|---|---|---|---|---|
| | C (%) | H (%) | N (%) | S (%) | Cl (%) |
| Theoretical | 34.40 | 3.75 | 25.07 | 11.48 | 12.69 |
| Measured | 34.49 | 3.70 | 24.73 | 11.11 | 12.89 |

Mass spectrum (m/z): 240 [(MH-Cl)+]

Nuclear magnetic resonance spectrum (DMSO-$d_6$.TMS internal standard): δ: 7.32 (1H, dd, J=8.6, 7.1 Hz), 7.55 (2H, brs), 7.90 (1H, dd, J=7.1, 0.9 Hz), 8.13 (1H, dd, J=8.6, 0.9 Hz), 9.65 (1 H,s), 10.20 (4H, br)

Example 8

One g of 10% palladium-carbon was added to a solution of 4.85 g of 5-nitro-2H-indazole-2-carboxamidine hydrochloride and 100 ml of methanol, with cooling with ice, and this was stirred in hydrogen atmosphere of normal pressure at the same temperature for 20 minutes. The reaction solution was filtered to remove the insoluble substances therefrom, and the solution was distilled under reduced pressure.

The residue was dissolved in methanol-ether, and 4N hydrogen chloride-1,4-dioxane solution was added thereto. The precipitated crystals were removed by filtration and recrystallized from methanol-ether to obtain 1.90 g of 5-amino-2H-indazole-2-carboxamidine dihydrochloride.
Physico-chemical properties:
Melting point: 177° to 178° C.

| Elementary analysis (as $C_8H_{11}N_5Cl_2.0.7H_2O$) | | | |
|---|---|---|---|
| | C (%) | H (%) | N (%) |
| Theoretical | 36.85 | 4.79 | 26.86 |
| Measured | 36.66 | 4.56 | 26.90 |

Mass spectrum (m/z): 176 [(M-2HCl)+]

Nuclear magnetic resonance spectrum (DMSO-$d_6$.TMS internal standard): δ: 5.80 (H, br), 7.38(1H, d, J=9.5 Hz), 7.65 (1H, s), 7.80 (1H, d, J=9.5 Hz), 9.39 (1H, s), 10.00 (4H, br)

In the same manner as in Example 8, compounds of the following Examples 9 and 10 were obtained.

Example 9

End product: 6-Amino-2H-indazole-2-carboxamidine dihydrochloride
Starting compound: 6-Nitro-2H-indazole-2-carboxamidine hydrochloride
Physico-chemical properties:
Melting point: 189° to 191° C.

| Elementary analysis (as $C_8H_{11}N_5Cl_2.0.3H_2O$): | | | |
|---|---|---|---|
| | C (%) | H (%) | N (%) |
| Theoretical | 37.90 | 4.61 | 27.62 |
| Measured | 38.14 | 4.36 | 27.81 |

Mass spectrum (m/z): 176 [(M-2HCl)+]

Nuclear magnetic resonance spectrum (DMSO-$d_6$.TMS internal standard): δ: 6.96 (1H, d, J=9.3 Hz), 7.08 (1H, s), 7.75 (1H, d, J=9.3 Hz), 7.95 (3H, brs), 9.34 (1H, s), 9.85 (4H, brs)

Example 10

End product: 7-Amino-2H-indazole-2-carboxamidine dihydrochloride
Starting compound: 7-Nitro-2H-indazole-2-carboxamidine hydrochloride
Physico-chemical properties:
Melting point: 195° to 198° C.

| Elementary analysis (as $C_8H_{11}N_5Cl_2.0.4H_2O$): | | | | |
|---|---|---|---|---|
| | C (%) | H (%) | N (%) | Cl (%) |
| Theoretical | 37.63 | 4.66 | 27.43 | 27.77 |
| Measured | 37.71 | 4.83 | 27.42 | 27.62 |

Mass spectrum (m/z): 176 [(MH-2HCl)+]

Nuclear magnetic resonance spectrum (DMSO-$d_6$.TMS internal standard): δ: 6.66–7.34 (3H, m), 7.68 (3H, brs), 9.34 (1H, s), 9.96 (4H, brs)

| Example No. | Chemical Structural Formula |
|---|---|
| 1 | Phenyl-CH=N-N(pyrazole)-C(=NH)-NH$_2$·HCl |
| 2 | 4-O$_2$N-phenyl-CH=N-N(pyrazole)-C(=NH)-NH$_2$·HCl |
| 3 | 3-O$_2$N-phenyl-CH=N-N(pyrazole)-C(=NH)-NH$_2$·HCl |
| 4 | 2-O$_2$N-phenyl-CH=N-N(pyrazole)-C(=NH)-NH$_2$·HCl |
| 5 | 4-HO-phenyl-CH=N-N(pyrazole)-C(=NH)-NH$_2$·HCl |
| 6 | 3-HO-phenyl-CH=N-N(pyrazole)-C(=NH)-NH$_2$·HCl |
| 7 | 2-H$_2$NO$_2$S-phenyl-CH=N-N(pyrazole)-C(=NH)-NH$_2$·HCl |
| 8 | 4-H$_2$N-phenyl-CH=N-N(pyrazole)-C(=NH)-NH$_2$·2HCl |
| 9 | 3-H$_2$N-phenyl-CH=N-N(pyrazole)-C(=NH)-NH$_2$·2HCl |
| 10 | 2-H$_2$N-phenyl-CH=N-N(pyrazole)-C(=NH)-NH$_2$·2HCl |

Example 11

A solution of 2.06 g of 3-propyl-2,4-pentanedione in 10 ml of methanol was added little by little to a solution of 1.56 g of aminoguanidine hydrochloride in 5 ml of water, 30 ml of methanol and 1 ml of concentrated hydrochloric acid, and stirred overnight at room temperature. The solvents were removed by distillation under reduced pressure, and the residue was purified by silica gel chromatography (eluent: chloroform/methanol=5/1) and then recrystallized from ethanol-ether to obtain 1.70 g of 3,5-dimethyl-4-propyl-1H-pyrazole-1-carboxamidine hydrochloride.

Physico-chemical properties:
Melting point: 204° to 206° C.
Mass: 180 (M-HCl)$^+$

| Elementary analysis (as $C_9H_{17}N_4Cl$): | | | | |
|---|---|---|---|---|
| | C (%) | H (%) | N (%) | Cl (%) |
| Theoretical | 49.88 | 7.91 | 25.85 | 16.36 |
| Measured | 49.88 | 7.92 | 25.97 | 16.26 |

Nuclear magnetic resonance spectrum (DMSO-d$_6$, TMS internal standard): δ: 0.88 (3H, t, J=7 Hz), 1.25–1.65 (2 H, m), 2.20 (3H, s), 2.26–2.49 (2H, m), 2.45 (3H, s), 9.30 (4H, brs)

In the same manner as in Example 11, compounds of the following Examples 12 to 34 were obtained.

Example 12

End product: 4-Butyl-3,5-dimethyl-1H-pyrazole-1-carboxamidine hydrochloride
Starting compound: 3-Butyl-2,4-pentanedione
Physico-chemical properties:
Melting point: 193° to 197° C.
Mass: 194 (M-HCl)$^+$

| Elementary analysis (as $C_{10}H_{19}N_4Cl$): | | | | |
|---|---|---|---|---|
| | C (%) | H (%) | N (%) | Cl (%) |
| Theoretical | 52.05 | 8.30 | 24.28 | 15.36 |
| Measured | 51.88 | 8.31 | 24.29 | 15.55 |

Nuclear magnetic resonance spectrum (DMSO-d$_6$, TMS internal standard): δ: 0.80–1.00 (3H, m), 1.17–1.60 (4H, m), 2.20 (3H, s), 2.28–2.49 (2H, m), 2.45 (3H, s), 9.31 (4H, brs)

Example 13

End product: 3,5-Dimethyl-4-(2-methylpropyl)-1H-pyrazole-1-carboxamidine hydrochloride
Starting compound: 3-Isobutyl-2,4-pentanedione
Physico-chemical properties:
Melting point: 212° to 214° C.
Mass: 194 (M-HCl)$^+$

| Elementary analysis (as $C_{10}H_{19}N_4Cl$): | | | | |
|---|---|---|---|---|
| | C (%) | H (%) | N (%) | Cl (%) |
| Theoretical | 52.05 | 8.30 | 24.28 | 15.36 |
| Measured | 51.91 | 8.24 | 24.30 | 15.21 |

Nuclear magnetic resonance spectrum (DMSO-d$_6$, TMS internal standard): δ: 0.87 (6H, d, J=6.6 Hz), 1.50–1.85 (1H, m), 2.19 (3H, s), 2.24 (2H, d, J=8.6 Hz), 2.43 (3H, s), 9.26 (4H, brs)

Example 14

End product: 3,5-Dimethyl-4-pentyl-1H-pyrazole-1-carboxamidine hydrochloride
Starting compound: 3-Pentyl-2,4-pentanedione
Physico-chemical properties:
Melting point: 184° to 186° C.
Mass: 208 (M-HCl)$^+$

| Elementary analysis (as $C_{11}H_{21}N_4Cl$): | | | | |
|---|---|---|---|---|
| | C (%) | H (%) | N (%) | Cl (%) |
| Theoretical | 53.98 | 8.65 | 22.89 | 14.48 |
| Measured | 53.82 | 8.45 | 22.91 | 14.37 |

Nuclear magnetic resonance spectrum (DMSO-$d_6$, TMS internal standard): δ: 0.79–0.93 (3H, m), 1.15–1.60 (6H, m), 2.20 (3H, s), 2.28–2.48 (2H, m), 2.43 (3H, s), 9.26 (4H, brs)

Example 15

End product: 4-Benzyl-3,5-dimethyl-1H-pyrazole-1-carboxamidine hydrochloride
Starting compound: 3-Benzyl-2,4-pentanedione
Physico-chemical properties:
Melting point: 191° to 195° C.
Mass: 228 (M-HCl)$^+$

| Elementary analysis (as $C_{13}H_{17}N_4Cl$): | | | | |
|---|---|---|---|---|
| | C (%) | H (%) | N (%) | Cl (%) |
| Theoretical | 58.98 | 6.47 | 21.16 | 13.39 |
| Measured | 58.84 | 6.44 | 21.21 | 13.48 |

Nuclear magnetic resonance spectrum (DMSO-$d_6$, TMS internal standard): δ: 2.11 (3H, s), 2.50 (3H, s), 3.79 (2H, s), 7.14–7.31 (5H, m), 9.31 (4H, brs)

Example 16

End product: 3,5-Dimethyl-4-(3-oxobutyl)-1H-pyrazole-1-carboxamidine hydrochloride
Starting compound: 3-Acetyl-2,6-heptanedione
Physico-chemical properties:
Melting point: 151° to 154° C.
Mass: 208 (M-HCl)$^+$

| Elementary analysis (as $C_{10}H_{17}N_4OCl.0.4 = 3H_2O$): | | | | |
|---|---|---|---|---|
| | C (%) | H (%) | N (%) | Cl (%) |
| Theoretical | 48.02 | 7.09 | 22.40 | 14.17 |
| Measured | 47.87 | 7.16 | 22.58 | 14.33 |

Nuclear magnetic resonance spectrum (DMSO-$d_6$, TMS internal standard): δ: 2.08 (3H, s), 2.21 (3H, s), 2.43 (3H, s), 2.43 (3H, s), 2.48–2.69 (4H, m), 9.23 (4H, brs)

Example 17

End product: Methyl 1-amidino-3,5-dimethyl-1H-pyrazole-4-propionate hydrochloride
Starting compound: Methyl 4-acetyl-5-oxohexanoate
Physico-chemical properties:
Melting point: 145° to 147° C.
Mass: 224 (M-HCl)$^+$

| Elementary analysis (as $C_{10}H_{17}N_4O_2Cl$): | | | | |
|---|---|---|---|---|
| | C (%) | H (%) | N (%) | Cl (%) |
| Theoretical | 46.07 | 6.57 | 21.49 | 13.60 |
| Measured | 45.88 | 6.53 | 21.51 | 13.72 |

Nuclear magnetic resonance spectrum (DMSO-$d_6$, TMS internal standard): δ: 2.22 (3H, s), 2.43 (3H, s), 2.44–2.77 (4H, m), 3.59 (3H, s), 9.25 (4H, brs)

Example 18

End product: 3-Methyl-4,5,6,7-tetrahydro-1H-indazole-1-carboxamidine hydrochloride
Starting compound: 2-Acetylcyclohexanone
Physico-chemical properties:
Melting point: 226° to 228° C.
Mass: 178 (M-HCl)$^+$

| Elementary analysis (as $C_9H_{15}N_4Cl$): | | | | |
|---|---|---|---|---|
| | C (%) | H (%) | N (%) | Cl (%) |
| Theoretical | 50.35 | 7.04 | 26.10 | 16.51 |
| Measured | 50.27 | 7.14 | 26.06 | 16.29 |

Nuclear magnetic resonance spectrum (DMSO-$d_6$, TMS internal standard): δ: 1.67–1.74 (4H, m), 2.18 (3H, s), 2.37–2.42 (2H, m), 2.88–2.91 (2H, m), 9.16 (4H, brs)

Example 19

End product: Methyl 1-amidino-3,5-dimethyl-1H-pyrazole-4-carboxylate hydrochloride
Starting compound: Methyl 2-acetylacetoacetate
Physico-chemical properties:
Melting point: 193° to 196° C.
Mass: 196 (M-HCl)$^+$

| Elementary analysis (as $C_8H_{13}N_4O_2Cl$): | | | | |
|---|---|---|---|---|
| | C (%) | H (%) | N (%) | Cl (%) |
| Theoretical | 41.30 | 5.63 | 24.08 | 15.24 |
| Measured | 40.90 | 5.57 | 24.07 | 15.16 |

Nuclear magnetic resonance spectrum (DMSO-$d_6$, TMS internal standard): δ: 2.40 (3H, s), 2.72 (3H, s), 3.82 (3H, s), 9.77 (4H, brs)

Example 20

End product: Methyl 1-amidino-3,5-dimethyl-1H-pyrazole-4-acetate hydrochloride
Starting compound: Methyl 3-acetyl-4-oxopentanoate
Physico-chemical properties:
Melting point: 185° to 187° C.
Mass: 210 (M-HCl)$^+$

| Elementary analysis (as $C_9H_{15}N_4O_2Cl$): | | | | |
|---|---|---|---|---|
| | C (%) | H (%) | N (%) | Cl (%) |
| Theoretical | 43.82 | 6.13 | 22.71 | 14.37 |
| Measured | 43.75 | 6.05 | 22.80 | 14.11 |

Nuclear magnetic resonance spectrum (DMSO-$d_6$, TMS internal standard): δ: 2.18 (3H, s), 2.44 (3H, s), 3.57 (2H, s), 3.63 (3H, s), 9.35 (4H, brs)

Example 21

End product: 3,5-Dimethyl-4-(4-nitrobenzyl)-1H-pyrazole-1-carboxamidine hydrochloride
Starting compound: 3-(4-Nitrobenzyl)-2,4-pentanedione
Physico-chemical properties:
Melting point: 185° to 188° C.
Mass: 273 (M-HCl)$^+$

| Elementary analysis (as $C_{13}H_{16}N_5O_2Cl$): | | | | |
|---|---|---|---|---|
| | C (%) | H (%) | N (%) | Cl (%) |
| Theoretical | 50.41 | 5.21 | 22.61 | 11.45 |
| Measured | 50.07 | 4.86 | 22.70 | 11.45 |

Nuclear magnetic resonance spectrum (DMSO-$d_6$, TMS internal standard): δ: 2.12 (3H, s), 2.51 (3H, s), 3.98 (2H, s), 7.44 (2H, d, J=8.5 Hz), 8.18 (2H, d, J=8.5 Hz), 9.32 (4H, brs)

Example 22

End product: 3,5-Dimethyl-4-(4-methoxybenzyl)-1H-pyrazole-1-carboxamidine hydrochloride
Starting compound: 3-(4-Methoxybenzyl)-2,4-pentanedione
Physico-chemical properties:
Melting point: 192° to 194° C.
Mass: 258 (M-HCl)$^+$

| Elementary analysis (as $C_{14}H_{19}N_4OCl$): | | | | |
|---|---|---|---|---|
| | C (%) | H (%) | N (%) | Cl (%) |
| Theoretical | 57.04 | 6.50 | 19.01 | 12.03 |
| Measured | 56.80 | 6.48 | 19.02 | 12.02 |

Nuclear magnetic resonance spectrum (DMSO-$d_6$, TMS internal standard): δ: 2.10 (3H, s), 2.48 (3H, s), 3.71 (5H, s), 6.78–7.12 (4H, m), 9.24 (4H, brs)

Example 23

End product: Ethyl 1-amidino-3,5-dimethyl-1H-pyrazole-4-carboxylate hydrochloride
Starting compound: Ethyl 2-acetylacetoacetate
Physico-chemical properties:
Melting point: 174° to 176° C.
Mass: 210 (M-HCl)$^+$

| Elementary analysis (as $C_9H_{15}N_4O_2Cl$): | | | | |
|---|---|---|---|---|
| | C (%) | H (%) | N (%) | Cl (%) |
| Theoretical | 43.82 | 6.13 | 22.71 | 14.37 |
| Measured | 43.79 | 6.06 | 22.87 | 14.50 |

Nuclear magnetic resonance spectrum (DMSO-$d_6$, TMS internal standard): δ: 1.31 (3H, t, J=7 Hz), 2.40 (3H, s), 2.72 (3H, s), 4.28 (2H, q, J=7 Hz), 9.74 (4H, brs)

Example 24

End product: Propyl 1-amidino-3,5-dimethyl-1H-pyrazole-4-carboxylate hydrochloride
Starting Compound: Propyl 2-acetylacetoacetate
Physico-chemical properties:
Melting point: 146° to 148° C.
Mass: 224 (M-HCl)$^+$

| Elementary analysis (as $C_{10}H_{17}N_4O_2Cl$): | | | | |
|---|---|---|---|---|
| | C (%) | H (%) | N (%) | Cl (%) |
| Theoretical | 46.07 | 6.57 | 21.49 | 13.60 |
| Measured | 45.83 | 6.85 | 21.59 | 13.55 |

Nuclear magnetic resonance spectrum (DMSO-$d_6$, TMS internal standard): δ: 0.97 (3H, t, J=7 Hz), 1.69–1.73 (2H, m), 2.40 (3H, s), 2.72 (3H, s), 4.20 (2H, t, J=6.5 Hz), 9.78 (4H, brs)

Example 25

End product: Butyl 1-amidino-3,5-dimethyl-1H-pyrazole-4-carboxylate hydrochloride
Starting compound: Butyl 2-acetylacetoacetate
Physico-chemical properties:
Melting point: 138° to 140° C.
Mass: 238 (M-HCl)$^+$

| Elementary analysis (as $C_{11}H_{19}N_4O_2Cl$): | | | | |
|---|---|---|---|---|
| | C (%) | H (%) | N (%) | Cl (%) |
| Theoretical | 48.09 | 6.97 | 20.39 | 12.90 |
| Measured | 47.91 | 6.95 | 20.41 | 12.92 |

Nuclear magnetic resonance spectrum (DMSO-$d_6$, TMS internal standard): δ: 0.93 (3H, t, J=7 Hz), 1.37–1.45 (2H, m), 1.65–1.70 (2H, m), 2.40 (3H, s), 2.70 (3H, s), 4.24 (2H, t, J=6.5 Hz), 9.69 (4H, brs)

Example 26

End product: Benzyl 1-amidino-3,5-dimethyl-1H-pyrazole-4-carboxylate hydrochloride
Starting compound: Benzyl 2-acetylacetoacetate
Physico-chemical properties:
Melting point: 160° to 162° C.
Mass: 272 (M-HCl)$^+$

| Elementary analysis (as $C_{14}H_{17}N_4O_2Cl$): | | | | |
|---|---|---|---|---|
| | C (%) | H (%) | N (%) | Cl (%) |
| Theoretical | 54.46 | 5.55 | 18.15 | 11.48 |
| Measured | 54.30 | 5.45 | 18.28 | 11.43 |

Nuclear magnetic resonance spectrum (DMSO-$d_6$, TMS internal standard): δ: 2.39 (3H, s), 2.71 (3H,s), 5.32 (2H, s), 7.35–7.47 (5H, m), 9.76 (4H, brs)

Example 27

End product: 3,5-Dimethyl-4-(3,4-methylenedioxybenzyl)-1H-pyrazole-1-carboxamidine hydrochloride Starting compound: 3-(3,4-Methylenedioxybenzyl)-2,4-pentanedione Physico-chemical properties:

Melting point: 181° to 183° C.

Mass: 272 (M-HCl)$^+$

| Elementary analysis (as $C_{14}H_{17}N_4O_2Cl\cdot 0.1H_2O$): | | | |
|---|---|---|---|
| | C (%) | H (%) | Cl (%) |
| Theoretical | 54.14 | 5.58 | 18.04 |
| Measured | 53.99 | 5.57 | 17.76 |

Nuclear magnetic resonance spectrum (DMSO-$d_6$, TMS internal standard): δ: 2.11 (3H, s), 2.46 (3H, s), 3.69 (2H, s), 5.96 (2H, s), 6.61–6.83 (3H, m), 9.11 (4H, brs)

Example 28

End product: 4-(4-Benzyloxybenzyl)-3,5-dimethyl-1H-pyrazole-1-carboxamidine hydrochloride Starting compound: 3-(4-benzyloxybenzyl)-2,4-pentanedione Physico-chemical properties:

Melting point: 197° to 199° C.

Mass: 334 (M-HCl)$^+$

Nuclear magnetic resonance spectrum (DMSO-$d_6$, TMS internal standard: δ: 2.10 (3H, s), 2.47 (3H, s), 3.71 (2H, s), 5.06 (2H, s), 6.93 (2H, d, J=8.5 Hz), 7.06 (H, d, J=8.5 Hz), 7.30–7.43 (5H, m), 9.17 (4H, brs)

Example 29

End product: 3,5-Dimethyl-4-(4-methoxycarbonylbenzyl)-1H-pyrazole-1-carboxamidine hydrochloride Starting compound: 3-(4-Methoxycarbonylbenzyl)-2,4-pentanedione Physico-chemical properties:

Melting point: 183° to 185° C.

Mass: 286 (M-HCl)$^+$

| Elementary analysis (as $C_{15}H_{19}N_4O_2Cl$): | | | | |
|---|---|---|---|---|
| | C (%) | H (%) | N (%) | Cl (%) |
| Theoretical | 55.81 | 5.93 | 17.36 | 10.98 |
| Measured | 55.71 | 5.86 | 17.44 | 11.00 |

Nuclear magnetic resonance spectrum (DMSO-$d_6$, TMS internal standard): δ: 2.10 (3H, s), 2.50 (3H, s), 3.83 (3H, s), 3.89 (2H, s), 7.31 (2H, d, J=8 Hz), 7.89 (2H, d, J=8 Hz), 9.32 (4H, brs)

Example 30

End product: 3,5-Dimethyl-4-(4-hydroxybenzyl)-1H-pyrazole-1-carboxamidine hydrochloride Starting compound: 3-(4-Hydroxybenzyl)-2,4-pentanedione Physico-chemical properties:

Melting point: 191° to 193° C.

Mass: 244 (M-HCl)$^+$

Elementary analysis (as $C_{13}H_{17}N_4OCl$):

| Elementary analysis (as $C_{13}H_{17}N_4OCl$): | | | | |
|---|---|---|---|---|
| | C (%) | H (%) | N (%) | Cl (%) |
| Theoretical | 55.61 | 6.10 | 19.96 | 12.63 |
| Measured | 55.41 | 6.11 | 19.89 | 12.71 |

Nuclear magnetic resonance spectrum (DMSO-$d_6$, TMS internal standard): δ: 2.09 (3H, s), 2.47 (3H, s), 3.65 (2H,s), 6.68 (2H, d, J=8.3 Hz), 6.93 (2H, d, J=8.3 Hz), 9.25 (4H, brs), 9.29 (1H, s)

Example 31

End product: 3,5-Dimethyl-4-(3,5-dimethyl-4-hydroxybenzyl)-1H-pyrazole-1-carboxamidine hydrochloride Starting compound: 3-(3,5-Dimethyl-4-hydroxybenzyl)-2,4-pentanedione Physico-chemical properties:

Melting point: 195° to 197° C.

Mass: 272 (M-HCl)$^+$

| Elementary analysis (as $C_{15}H_{21}N_4OCl$): | | | | |
|---|---|---|---|---|
| | C (%) | H (%) | N (%) | Cl (%) |
| Theoretical | 58.34 | 6.85 | 18.14 | 11.48 |
| Measured | 58.12 | 6.82 | 18.29 | 11.47 |

Nuclear magnetic resonance spectrum (DMSO-$d_6$, TMS internal standard): δ: 2.09 (3H, s), 2.10 (6H, s), 2.47 (3H, s), 3.59 (2h, S), 6.66 (2H, s), 8.04 (1H, s), 9.24 (4H, brs)

Example 32

End product: 4- (3,5-Di-tert-butyl-4-hydroxybenzyl) -3,5-dimethyl-1H-pyrazole-1-carboxamidine hydrochloride Starting compound: 3-(3,5-Di-tert-butyl-4-hydroxybenzyl)-2,4-pentanedione Physico-chemical properties:

Melting point: 195° to 197° C.

Mass: 356 (M-HCl)$^+$

| Elementary analysis (as $C_{21}H_{33}N_4OCl.0.2H_2O$): | | | | |
|---|---|---|---|---|
| | C (%) | H (%) | N (%) | Cl (%) |
| Theoretical | 63.60 | 8.49 | 14.13 | 8.94 |
| Measured | 63.32 | 8.38 | 14.12 | 9.16 |

Nuclear magnetic resonance spectrum (DMSO-$d_6$, TMS internal standard): δ: 1.34 (18H, s), 2.18 (3H, s), 2.49 (3H, s), 3.65 (2H, s), 6.80 (1H, s), 6.90 (2H, s), 9.19 (4H, brs)

Example 33

End product: 2-Methoxyethyl 1-amidino-3,5-dimethyl-1H-pyrazole-1-carboxylate hydrochloride
Starting compound: 2-Methoxyethyl 2-acetylacetoacetate
Physico-chemical properties:
Melting point: 123° to 125° C.
Mass: 241 (M-HCl)$^+$

| Elementary analysis (as $C_{10}H_{17}N_4O_3Cl$): | | | | |
|---|---|---|---|---|
| | C (%) | H (%) | N (%) | Cl (%) |
| Theoretical | 43.40 | 6.19 | 20.25 | 12.81 |
| Measured | 43.11 | 6.06 | 20.23 | 13.02 |

Nuclear magnetic resonance spectrum (DMSO-$d_6$, TMS internal standard): δ: 2.40 (3H, s), 2.71 (3H, s), 3.30 (3H, s), 3.64 (2H, t, J=4.6 Hz), 9.71 (4H, brs)

Example 34

End product: 2-Ethoxyethyl 1-amidino-3,5-dimethyl-1H-pyrazole-1-carboxylate hydrochloride
Starting compound: 2-Ethoxyethyl 2-acetylacetoacetate
Physico-chemical properties:
Melting point: 120° to 122° C.
Mass: 255 (M-HCl)$^+$ Nuclear magnetic resonance spectrum (DMSO-$d_6$, TMS internal standard): δ: 1.12 (3H, t, J=7 Hz), 2.40 (3H, s), 2.72 (3H, s), 3.49 (2H, q, J=7 Hz), 3.67 (2H, t, J=4, 9 Hz), 4.34 (2H, t, J=4.9 Hz), 9.73 (4H, brs)

Example 35

(1) 1.86 g of aminoguanidine hydrochloride were added to a solution of 3.0 g of triacetylmethane and 30 ml of methanol with cooling at −10° C., and the reaction mixture was stirred for one day with cooling with ice. The solvent was removed by distillation under reduced pressure, and the resulting residue was purified by silica gel chromatography (eluent: chloroform/methanol=5/1) and then recrystallized from ether-chloroform to obtain 484 mg of 4-acetyl-3,5-dimethyl-1H-pyrazole-1-carboxamidine.
Physico-chemical properties:
Nuclear magnetic resonance spectrum (DMSO-$d_6$, TMS internal standard): δ: 2.38 (3H, s), 2.42 (3H, s), 2.76 (3H, s), 6.54 (3H, brs)

(2) 0.7 ml of 4N-hydrochloric acid-1,4-dioxane solution were dropwise added to a solution of 484 mg of 4-acetyl-3,5-dimethyl-1H-pyrazole-1-carboxamidine in 1 ml of ethanol and 5 ml of ether. The crystals precipitated out were taken out by filtration to obtain 488 mg of 4-acetyl-3,5-dimethyl-1H-pyrazole-1-carboxamidine hydrochloride.

Physico-chemical properties:
Melting point: 164° to 166° C.
Mass: 180 (M-HCl)$^+$

| Elementary analysis (as $C_8H_{13}N_4Cl$): | | | |
|---|---|---|---|
| | C (%) | H (%) | N (%) |
| Theoretical | 44.35 | 6.05 | 25.86 |
| Measured | 44.30 | 6.07 | 25.67 |

Example 36

2 g of nitronium tetrafluoroborate were added little by little to a suspension of 2.01 g of 3,5-dimethyl-1H-pyrazole-1-carboxamidine nitrate in 150 ml of absolute acetonitrile, with cooling with ice in argon atmosphere, and the reaction mixture was stirred for 30 minutes with cooling with ice. The solvent was removed by distillation under reduced pressure, and the residue was washed with chloroform to obtain 2.43 g of 3,5-dimethyl-4-nitro-1H-pyrazole-1-carboxamidine nitrate.
Physico-chemical properties:
Mass: 183 (M-HNO$_3$)
Nuclear magnetic resonance spectrum (DMSO-$d_6$, TMS internal standard): δ: 2.51 (3H, s), 2.77 (3H, s), 9.83 (4H, brs)

Example 37

500 mg of 10% palladium-carbon were added to a solution of 984 mg of 3,5-dimethyl-4-nitro-1H-pyrazole-1-carboxamidine nitrate in 20 ml of methanol, and stirred for 45 minutes in hydrogen atmosphere of normal pressure with cooling with ice. The reaction solution was filtered to remove the insoluble solids therefrom, and the solvent was removed by distillation under reduced pressure. The resulting residue was dissolved in 5 ml of water, 160 mg of sodium hydroxide were added thereto, and the mixture was extracted with chloroform.

The organic layer was dried with anhydrous sodium sulfate, and the solvent was removed by distillation under reduced pressure. The resulting residue was dissolved in 5 ml of ethanol and 2 ml of 4N-hydrochloric acid-1,4-dioxane solution, and the solvents were removed by distillation under reduced pressure. The resulting residue was recrystallized from ethanol-ether-chloroform to obtain 810 mg of 4-amino-3,5-dimethyl-1H-pyrazole-1-carboxamidine dihydrochloride.

Physico-chemical properties:
Melting point: 167° to 169° C.
Mass: 153 (M-2HCl)+

| Elementary analysis (as $C_6H_{13}N_5Cl_2.0.5H_2O$): | | | |
|---|---|---|---|
| | C (%) | H (%) | N (%) |
| Theoretical | 30.65 | 6.00 | 29.79 |
| Measured | 30.74 | 5.97 | 30.10 |

Nuclear magnetic resonance spectrum (DMSO-$d_6$.TMS internal standard): δ: 2.34 (3H, s), 2.62 (3H,s), 9.58 (7H, brs)

Example 38

In the same manner as in Example 37, the following compound was obtained.

End product: 4-(4-Aminobenzyl)-3,5-dimethyl-1H-pyrazole-1-carboxamidine dihydrochloride Starting compound: 3,5-Dimethyl-4-(4-nitrobenzyl)-1H-pyrazole-1-carboxamidine hydrochloride Physico-chemical properties:

Melting point: 213° to 217° C.

Mass: 243 (M-2HCl)+

Elementary analysis (as $C_{13}H_{19}N_5Cl_2 \cdot 0.2H_2O$):

|  | C (%) | H (%) | N (%) | Cl (%) |
|---|---|---|---|---|
| Theoretical | 48.82 | 6.11 | 21.90 | 22.17 |
| Measured | 48.75 | 6.12 | 21.66 | 22.16 |

Nuclear magnetic resonance spectrum (DMSO-$d_6$.TMS internal standard): δ: 2.12 (3H, s), 2.50 (3H, s), 3.54 (2H, brs), 3.81 (2H, s), 7.24–7.30 (4H, m), 9.25 (3H, brs), 10.31 (2H, brs)

Example 39

A solution of 0.17 g of cyanamide in 0.3 ml of water was added to a solution of 0.46 g of 4-(3-chloropropyl)-3,5-dimethyl-1H-pyrazole hydrochloride in 5 ml of ethanol, and the reaction mixture was stirred for one day at 80° C. the solvent was removed by distillation under reduced pressure, and the resulting residue was recrystallized from isopropanol-diisopropylether to obtain 0.13 g of 4-(3-chloropropyl)-3,5 -dimethyl-1H-pyrazole-1-carboxamidine hydrochloride.

Physico-chemical properties:

Melting point: 183° to 185° C.

Mass: 214, 216 (M-HCl)+

Nuclear magnetic resonance spectrum (DMSO-$d_6$.TMS internal standard): δ: 1.69–2.11 (2H, m), 2.22 (3H, s), 2.44 (3H, s), 2.48–2.60 (2H, m), 3.50–3.11 (2H, m), 9.27 (4H, brs)

Example 40

In the same manner as in Example 39, the following compound was obtained.

End product: 3,5-Dimethyl-4-(3-methoxypropyl)01H-pyrazole-1-carboxamidine hydrochloride Starting compound: 3,5-Dimethyl-4-(3-methoxypropyl)-1H-pyrazole hydrochloride Physico-chemical properties:

Melting point: 155° to 157° C.

Mass: 211 (MH-HCl)+

Nuclear magnetic resonance spectrum (DMSO-$d_6$.TMS internal standard): δ: 1.48–1.78 (2H, m), 2.20 (3H, s), 2.33–2.54 (2H, m), 2.42 (3H, s), 3.24 (3N, s), 3.21–3.35 (2H, m), 9.22 (4H, brs)

Example 41

A catalytic amount of 10% palladium-carbon was added to a solution of 1.74 g of benzyl 1-amidino-3,6-dimethyl-1H-pyrazole-4-carboxylate hydrochloride in 40 ml of methanol, and stirred for 15 minutes in hydrogen atmosphere of normal pressure at room temperature. The reaction solution was filtered to remove the insoluble solids therefrom, and the solvent was removed by distillation under reduced pressure. The resulting residue as recrystallized from ethanol-ether to obtain 1.11 g of 1-amidino-3,5-dimethyl-1H-pyrazole-4-carboxylic acid hydrochloride.

Physico-chemical properties:

Melting point: 201° to 203° C.

Mass: 182 (M-HCl)+

Elementary analysis (as $C_7H_{11}N_4O_2Cl \cdot 0.1H_2O$):

|  | C (%) | H (%) | N (%) | Cl (%) |
|---|---|---|---|---|
| Theoretical | 38.14 | 5.12 | 25.42 | 16.08 |
| Measured | 38.05 | 5.01 | 25.70 | 16.35 |

Nuclear magnetic resonance spectrum (DMSO-$d_6$.TMS internal standard): δ: 2.39 (3H, s), 2.72 (3H, s), 9.76 (4H, brs)

Example 42

0.49 g of chloroamidine hydrochloride were added to a solution of 0.82 g of N-butyl-3,5-dimethyl-1H-pyrazole-4-carboxamide in 30 ml of dioxane, and the reaction mixture was heated at 100° C. for 4 hours. After cooling to room temperature, the product was taken out by filtration. The crude crystals thus obtained were recrystallized from ethanol-diethyl ether to obtain 0.54 g of N-butyl-1-amidino-3,5-dimethyl-2H-pyrazole-4-carboxamide hydrochloride.

Physico-chemical properties:

Melting point: 182° to 184° C.

Mass: 238 (MH-HCl)+

Elementary analysis (as $C_{11}H_{20}N_5OCl \cdot 0.1H_2O$):

|  | C (%) | H (%) | N (%) | Cl (%) |
|---|---|---|---|---|
| Theoretical | 47.95 | 7.39 | 25.41 | 12.87 |
| Measured | 47.93 | 7.31 | 25.61 | 12.98 |

Nuclear magnetic resonance spectrum (DMSO-$d_6$.TMS internal standard): δ: 0.91 (3H, t, J=7.3 Hz), 1.30–1.36 (2H, m), 1.45–1.52 (2H, m), 2.31 (3H, s), 2.55 (3H, s), 3.19–3.24 (2H, m), 8.10 (1H, t, J=5.5 Hz), 9.50 (4H, brs)

Example 43

In the same manner as in Example 42, the following compound was obtained.

End product: 3,5-Dimethyl-4-fluoro-1H-pyrazole-1-carboxamidine hydrochloride

Starting compound: 3,5-Dimethyl-4-fluoro-1H-pyrazole

Physico-chemical properties:

Melting point: 168° to 169° C.

Mass: 157 (MH-HCl)+

Nuclear magnetic resonance spectrum (DMSO-$d_6$.TMS internal standard): δ: 2.26 (3H, s), 2.47 (3H, d, J=2.4 Hz), 9.42 (4H, brs)

Example 44

5 ml of pyridine were added to a solution of 0.86 g of 4-amino-3,5-dimethyl-1H-pyrazole-1-carboxamidine dihydrochloride in 20 ml of dimethylformamide with cooling with ice, and successively 0.5 ml of valeryl chloride were dropwise added thereto. The reaction mixture was stirred overnight at 4° C., and 2 ml of methanol were added thereto. The solvent was removed by distillation under reduced pressure, and the resulting residue was diluted with 1N-sodium hydroxide and then extracted with chloroform. The organic layer was dried with anhydrous sodium sulfate, and the solvent was reduced by distillation under reduced pressure.

The residue thus obtained was purified by silica gel chromatography (eluent: chloroform/methanol=5/1) and was converted into its hydrochloride, which was then recrystallized from ethanol-diethyl ether to obtain 0.53 g of 3,5-dimethyl-4-pentanamido-1H-pyrazole-1-carboxamidine hydrochloride.

Physico-chemical properties:

Melting point: 178° to 180° C.

Mass: 238 (MH-HCl)+

| Elementary analysis (as $C_{11}H_{20}N_5OCl$): | | | | |
|---|---|---|---|---|
| | C (%) | H (%) | N (%) | Cl (%) |
| Theoretical | 48.26 | 7.36 | 25.58 | 12.95 |
| Measured | 48.00 | 7.27 | 25.71 | 13.21 |

Nuclear magnetic resonance spectrum (DMSO-$d_6$.TMS internal standard): δ: 0.91 (3H, t, J=7.3 Hz), 1.29–1.38 (2H, m), 1.54–1.61 (2H, m), 2.11 (3H, s), 2.32 (2H, t, J=7.3 Hz), 2.34 (3H, s), 9.31 (4H, brs), 9.52 (1H, s)

Example 45

In the same manner as in Example 44, the following compound was obtained.

End product: 3,5-Dimethyl-4-ethoxycarbonylamino-1H-pyrazole-1-carboxamidine hydrochloride Starting compound: Ethyl chloroformate Physico-chemical properties:

Melting point: 193° to 195° C.

Mass: 225 (M-HCl)+

| Elementary analysis (as $C_9H_{16}N_5O_2Cl$): | | | | |
|---|---|---|---|---|
| | C (%) | H (%) | N (%) | Cl (%) |
| Theoretical | 41.30 | 6.16 | 26.76 | 13.55 |
| Measured | 41.07 | 6.06 | 26.75 | 13.56 |

Nuclear magnetic resonance spectrum (DMSO-$d_6$.TMS internal standard): δ: 1.20–1.26 (3H, m), 2.14 (3H, s), 2.36 (3H, s), 4.08–4.13 (2H, m), 8.96 (1H, brs), 9.34 (4H, brs)

TABLE 3

Formula for Examples 11–45

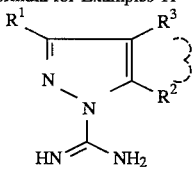

| Example No. | $R^1$ | $R^2$ | $R^3$ | Salt |
|---|---|---|---|---|
| 11 | $CH_3$ | $CH_3$ | $CH_3(CH_2)_2-$ | HCl |
| 12 | $CH_3$ | $CH_3$ | $CH_3(CH_2)_3-$ | HCl |
| 13 | $CH_3$ | $CH_3$ | $(CH_3)_2CHCH_2-$ | HCl |
| 14 | $CH_3$ | $CH_3$ | $CH_3(CH_2)_5-$ | HCl |
| 15 | $CH_3$ | $CH_3$ | $\phi\text{-}CH_2-$ | HCl |
| 16 | $CH_3$ | $CH_3$ | $CH_3\overset{O}{\overset{\|}{C}}(CH_2)_2$ | HCl |
| 17 | $CH_3$ | $CH_3$ | $CH_3O\overset{O}{\overset{\|}{C}}(CH_2)_2-$ | HCl |
| 18 | $CH_3$ | \multicolumn{2}{c}{$-(CH_2)_4-$} | HCl |
| 19 | $CH_3$ | $CH_3$ | $CH_3O\overset{O}{\overset{\|}{C}}-$ | HCl |
| 20 | $CH_3$ | $CH_3$ | $CH_3O\overset{O}{\overset{\|}{C}}CH_2-$ | HCl |
| 21 | $CH_3$ | $CH_3$ | $O_2N\text{-}C_6H_4\text{-}CH_2-$ | HCl |
| 22 | $CH_3$ | $CH_3$ | $CH_3O\text{-}C_6H_4\text{-}CH_2-$ | HCl |

TABLE 3-continued

Formula for Examples 11–45

| Example No. | R¹ | R² | R³ | Salt |
|---|---|---|---|---|
| 23 | $CH_3$ | $CH_3$ | $CH_3-CH_2OC(=O)-$ | HCl |
| 24 | $CH_3$ | $CH_3$ | $CH_3(CH_2)_2OC(=O)-$ | HCl |
| 25 | $CH_3$ | $CH_3$ | $CH_3(CH_2)_3OC(=O)-$ | HCl |
| 26 | $CH_3$ | $CH_3$ | $C_6H_5-CH_2OC(=O)-$ | HCl |
| 27 | $CH_3$ | $CH_3$ | 3,4-methylenedioxybenzyl ($-CH_2-$) | HCl |
| 28 | $CH_3$ | $CH_3$ | $C_6H_5-CH_2O-C_6H_4-CH_2-$ | HCl |
| 29 | $CH_3$ | $CH_3$ | $CH_3OC(=O)-C_6H_4-CH_2-$ | HCl |
| 30 | $CH_3$ | $CH_3$ | $HO-C_6H_4-CH_2-$ | HCl |
| 31 | $CH_3$ | $CH_3$ | 3,5-dimethyl-4-hydroxybenzyl | HCl |
| 32 | $CH_3$ | $CH_3$ | 3,5-di-tert-butyl-4-hydroxybenzyl | HCl |
| 33 | $CH_3$ | $CH_3$ | $CH_3O(CH_2)_2OC(=O)-$ | HCl |
| 34 | $CH_3$ | $CH_3$ | $CH_3CH_2O(CH_2)_2OC(=O)-$ | HCl |
| 35 | $CH_3$ | $CH_3$ | $CH_3C(=O)-$ | HCl |
| 36 | $CH_3$ | $CH_3$ | $NO_2$ | $HNO_3$ |

TABLE 3-continued

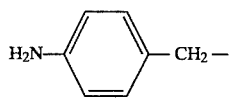

Formula for Examples 11–45

| Example No. | R¹ | R² | R³ | | Salt |
|---|---|---|---|---|---|
| 37 | $CH_3$ | $CH_3$ | $NH_2$ | | HCl |
| 38 | $CH_3$ | $CH_3$ | $H_2N-\langle\bigcirc\rangle-CH_2-$ | | 2HCl |
| 39 | $CH_3$ | $CH_3$ | $Cl-(CH_2)_3-$ | | HCl |
| 40 | $CH_3$ | $CH_3$ | $CH_3O(CH_2)_3-$ | | HCl |

Example 46

A solution of 1.26 g of pivaloylacetonitrile and 1.37 g of aminoguanidine hydrochloride in 15 ml of methanol and 15 ml of acetic acid was heated under reflux for 5 hours. The solvents were removed by distillation under reduced pressure, and the resulting residue was purified by silica gel chromatography (eluent: chloroform/methanol=5/1) and then recrystallized from ethanol-ether to obtain 0.74 g of 5-amino-3-(1,1-dimethylethyl)-1H-pyrazole-1-carboxamidine hydrochloride having the following physico-chemical properties:

Melting point: 197° to 201° C.
Mass: 181 (M-HCl)⁺

| Elementary analysis (as $C_8H_{16}N_5Cl \times 0.1H_2O$) | | | | |
|---|---|---|---|---|
| | C (%) | H (%) | N (%) | Cl (%) |
| Theoretical | 43.78 | 7.44 | 31.91 | 16.15 |
| Measured | 43.71 | 7.36 | 32.08 | 16.31 |

Nuclear magnetic resonance spectrum (DMSO-$d_6$, TMS internal standard): δ: 1.22 (H, s), 5.59 (1H, s), 8.79 (4H, br)

In the same manner as in Example 46, compounds of the following Examples 47 to 63 were obtained.

Example 47

End product: 5-Amino-3-(2-phenylethenyl)-1H-pyrazole-1-carboxamidine hydrochloride
Starting compound: Cinnamoylacetonitrile
Physico-chemical properties:
Melting point: 209° to 210° C.
Mass: 227 (M-HCl)⁺

| Elementary analysis (as $C_{12}H_{14}N_5Cl$) | | | | |
|---|---|---|---|---|
| | C (%) | H (%) | N (%) | Cl (%) |
| Theoretical | 54.65 | 5.35 | 26.56 | 13.44 |
| Measured | 54.56 | 5.32 | 26.50 | 13.24 |

Nuclear magnetic resonance spectrum (DMSO-$d_6$, TMS internal standard): δ: 5.99 (1H, s), 6.87–7.68 (7H, m), 9.01 (4H, br)

Example 48

End product: 5-Amino-3-(2-thienyl)-1H-pyrazole-1-carboxamidine hydrochloride
Starting compound: 2-Thienoylacetonitrile
Physico-chemical properties:
Melting point: 179° to 182° C.
Mass: 207 (M-HCl)⁺

| Elementary analysis (as $C_8H_{10}N_5OClS \times 0.4H_2O$) | | | | |
|---|---|---|---|---|
| | C (%) | H (%) | N (%) | Cl (%) |
| Theoretical | 38.29 | 4.34 | 27.91 | 14.13 |
| Measured | 38.60 | 4.12 | 27.65 | 14.24 |

Nuclear magnetic resonance spectrum (DMSO-$d_6$, TMS internal standard): δ: 5.98 (1H, s), 7.09–7.19 (1H, m), 7.54–7.66 (2H, m), 8.95 (4H, br)

Example 49

End product: 5-Amino-3-(2-furyl)-1H-pyrazole-1-carboxamidine hydrochloride
Starting compound: 2-Furoylacetonitrile
Physico-chemical properties:
Melting point: 187° to 190° C.
Mass: 191 (M-HCl)⁺

| Elementary analysis (as $C_8H_{10}N_5OCl$) | | | | |
|---|---|---|---|---|
| | C (%) | H (%) | N (%) | Cl (%) |
| Theoretical | 42.21 | 4.43 | 30.76 | 15.57 |
| Measured | 41.81 | 4.39 | 30.75 | 15.38 |

Nuclear magnetic resonance spectrum (DMSO-$d_6$, TMS internal standard): δ: 5.92 (1H, s), 6.60–6.65 (1H, m), 6.94–6.98 (1H, m), 7.81 (1H, d, J=1 Hz), 9.21 (4H, br)

Example 50

End product: 5-Amino-3-(2-methyl-3-furyl)-1H-pyrazole-1-carboxamidine hydrochloride Starting compound: (2-Methyl-3-furoyl)acetonitrile Physico-chemical properties:

Melting point: 178° to 181° C.

Mass: 205 (M-HCl)$^+$

| Elementary analysis (as $C_9H_{12}N_5OCl \times 0.1H_2O$) | | | | |
|---|---|---|---|---|
| | C (%) | H (%) | N (%) | Cl (%) |
| Theoretical | 44.40 | 5.05 | 28.76 | 14.56 |
| Measured | 44.44 | 5.01 | 28.51 | 14.26 |

Nuclear magnetic resonance spectrum (DMSO-$d_6$, TMS internal standard): δ: 2.52 (3H, s), 5.85 (1H, s), 6.75 (1H, d, J=2 Hz), 7.57 (1H, d, J=2 Hz), 9.02 (4H, br)

Example 51

End product: 5-Amino-3-(4-methylphenyl)-1H-pyrazole-1-carboxamidine hydrochloride Starting compound: (4-Methylbenzoyl)acetonitrile Physico-chemical properties:

Melting point: 178° to 181° C.

Mass: 215 (M-HCl)$^+$

| Elementary analysis (as $C_{11}H_{14}N_5Cl \times 0.2H_2O$) | | | | |
|---|---|---|---|---|
| | C (%) | H (%) | N (%) | Cl (%) |
| Theoretical | 51.75 | 5.68 | 27.43 | 13.89 |
| Measured | 51.92 | 5.67 | 27.03 | 13.97 |

Nuclear magnetic resonance spectrum (DMSO-$d_6$, TMS internal standard): δ: 2.35 (3H, s), 6.07 (1H, s), 7.27 (2H, d, J=8 Hz), 7.77 (2H, d, J=8 Hz), 8.88 (4H, br)

Example 52

End product: 5-Amino-3-(3-trifluoromethylphenyl)-1H-pyrazole-1-carboxamidine hydrochloride Starting compound: (3-Trifluoromethylbenzoyl)acetonitrile Physico-chemical properties:

Melting point: 209° to 212° C.

Mass: 269 (M-HCl)$^+$

| Elementary analysis (as $C_{11}H_{11}N_5OClS \times 0.4H_2O$) | | | | |
|---|---|---|---|---|
| | C (%) | H (%) | N (%) | Cl (%) |
| Theoretical | 43.22 | 3.63 | 22.91 | 18.64 |
| Measured | 43.02 | 3.61 | 22.98 | 18.42 |

Nuclear magnetic resonance spectrum (DMSO-$d_6$, TMS internal standard): δ: 6.23 (1H, s), 7.61–7.77 (2H, m), 8.13–8.26 (2H, m), 9.17 (4H, br)

Example 53

End product: 5-Amino-3-(4-trifluoromethylphenyl)-1H-pyrazole-1-carboxamidine hydrochloride Starting compound: (4-Trifluoromethylbenzoyl)acetonitrile Physico-chemical properties:

Melting point: 189° to 192° C.

Mass: 269 (M-HCl)$^+$

| Elementary analysis (as $C_{11}H_{11}N_5F_3Cl$) | | | | | |
|---|---|---|---|---|---|
| | C (%) | H (%) | N (%) | Cl (%) | F (%) |
| Theoretical | 43.22 | 3.63 | 22.91 | 11.60 | 18.64 |
| Measured | 42.91 | 3.62 | 23.01 | 11.53 | 18.47 |

Nuclear magnetic resonance spectrum (DMSO-$d_6$, TMS internal standard): δ: 6.18 (2H, s), 6.44 (2H, br), 7.83 (2H, d, J=8.5 Hz), 8.10 (2H, d, J=8.5 Hz), 9.29 (4H, brs)

Example 54

End product: 5-Amino-3-(4-methoxyphenyl)-1H-pyrazole-1-carboxamidine hydrochloride Starting compound: (4-Methoxybenzoyl)acetonitrile Physico-chemical properties:

Melting point: 184° to 187° C.

Mass: 231 (M-HCl)$^+$

| Elementary analysis (as $C_{11}H_{14}N_5OCl$) | | | | |
|---|---|---|---|---|
| | C (%) | H (%) | N (%) | Cl (%) |
| Theoretical | 49.35 | 5.27 | 26.16 | 13.24 |
| Measured | 49.16 | 5.35 | 25.97 | 13.23 |

Nuclear magnetic resonance spectrum (DMSO-$d_6$, TMS internal standard): δ: 3.80 (3H, s), 6.04 (1H, s), 7.01 (2H, d, J=9 Hz), 7.81 (2H, d, J=9 Hz), 9.02 (4H, br)

Example 55

End product: 5-Amino-3-(4-trifluoromethoxyphenyl)-1H-pyrazole-1-carboxamidine hydrochloride Starting compound: (4-Trifluoromethoxybenzoyl)acetonitrile Physico-chemical properties:

Melting point: 182° to 185° C.

Mass: 285 (M-HCl)$^+$

| Elementary analysis (as $C_{11}H_{11}N_5ClF_3O \times 0.4H_2O$) | | | | |
|---|---|---|---|---|
| | C (%) | H (%) | N (%) | Cl (%) |
| Theoretical | 40.17 | 3.62 | 21.29 | 10.78 |
| Measured | 40.36 | 3.61 | 21.00 | 10.62 |

Nuclear magnetic resonance spectrum (DMSO-$d_6$, TMS internal standard): δ: 6.13 (1H, s), 6.43 (2H, brs), 7.46 (2H, d, J=8 Hz), 8.01 (2H, d, J=8 Hz), 9.27 (4H, br)

Example 56

End product: 5-Amino-3-(4-fluorophenyl)-1H-pyrazole-1-carboxamidine hydrochloride
Starting compound: (4-Fluorobenzoyl)acetonitrile
Physico-chemical properties:
Melting point: 194° to 198° C.
Mass: 219 (M-HCl)$^+$

| Elementary analysis (as $C_{10}H_{11}N_5ClF \times 0.2H_2O$) | | | | | |
|---|---|---|---|---|---|
| | C (%) | H (%) | N (%) | Cl (%) | F (%) |
| Theoretical | 46.32 | 4.43 | 27.01 | 13.67 | 7.33 |
| Measured | 46.11 | 4.31 | 27.09 | 13.55 | 7.25 |

Nuclear magnetic resonance spectrum (DMSO-$d_6$, TMS internal standard): δ: 6.09 (1H, s), 7.20–7.40 (2H, m), 7.85–8.02 (2H, m), 9.05 (4H, br)

Example 57

End product: 5-Amino-3-(3-chlorophenyl)-1H-pyrazole-1-carboxamidine hydrochloride
Starting compound: (3-Chlorobenzoyl)acetonitrile
Physico-chemical properties:
Melting point: 192° to 194° C.
Mass: 235 (M-HCl)$^+$
Nuclear magnetic resonance spectrum (DMSO-$d_6$, TMS internal standard): δ: 6.16 (1H, s), 6.42 (2H, br), 7.49–7.52 (2H, m), 7.82–7.84 (1H, m), 7.99 (1H, s), 9.25 (4H, br)

Example 58

End product: 5-Amino-3-(4-chlorophenyl)-1H-pyrazole-1-carboxamidine hydrochloride
Starting compound: (4-Chlorobenzoyl)acetonitrile
Physico-chemical properties:
Melting point: 192° to 195° C.
Mass: 235 (M-HCl)$^+$
Nuclear magnetic resonance spectrum (DMSO-$d_6$, TMS internal standard): δ: 6.11 (1H, s), 7.53 (2H, d, J=8.5 Hz), 7.91 (2H, d, J=8.5 Hz), 9.21 (4H, br)

Example 59

End product: 5-Amino-3-(4-nitrophenyl)-1H-pyrazole-1-carboxamidine hydrochloride
Starting compound: (4-Nitrobenzoyl)acetonitrile
Physico-chemical properties: Melting point: 205° to 207° C.
Mass: 246 (M-HCl)$^+$

| Elementary analysis (as $C_{10}H_{11}N_6O_2Cl$) | | | | |
|---|---|---|---|---|
| | C (%) | H (%) | N (%) | Cl (%) |
| Theoretical | 42.49 | 3.92 | 29.73 | 12.54 |
| Measured | 42.26 | 3.81 | 29.84 | 12.53 |

Nuclear magnetic resonance spectrum (DMSO-$d_6$, TMS internal standard): δ: 6.22 (1H, s), 8.15 (2H, d, J=8.5 Hz), 8.32 (2H, d, J=8.5 Hz), 9.31 4H, br)

Example 60

End product: 5-Amino-3-(3,4-dimethoxyphenyl)-1H-pyrazole-1-carboxamidine hydrochloride
Starting compound: (3,4-Dimethoxybenzoyl)acetonitrile
Physico-chemical properties:
Melting point: 208° to 210° C.
Mass: 261 (M-HCl)$^+$

| Elementary analysis (as $C_{12}H_{16}N_5O_2Cl$) | | | | |
|---|---|---|---|---|
| | C (%) | H (%) | N (%) | Cl (%) |
| Theoretical | 48.41 | 5.42 | 23.52 | 11.91 |
| Measured | 48.34 | 5.46 | 23.45 | 11.86 |

Nuclear magnetic resonance spectrum (DMSO-$d_6$, TMS internal standard): δ: 3.80 (3H, s), 3.83 (3H, s), 6.08 (1H, s), 7.02 (1H, d, J=8 Hz), 7.39 (1H, d, J=8 Hz), 7.48 (1H, s), 9.07 (4H, br)

Example 61

End product: 5-Amino-3-(3,4,5-trimethoxyphenyl)-1H-pyrazole-1-carboxamidine hydrochloride
Starting compound: (3,4,5-Trimethoxybenzoyl)acetonitrile
Physico-chemical properties:
Melting point: 199° to 202° C.
Mass: 291 (M-HCl)$^+$
Nuclear magnetic resonance spectrum (DMSO-$d_6$, TMS internal standard): δ: 3.68 (3H, s), 3.83 (6H, s), 6.31 (1H, s), 7.22 (2H, s), 7.98 (4H, br)

Example 62

End product: 5-Amino-3-(3-methylphenyl)-1H-pyrazole-1-carboxamidine hydrochloride
Starting compound: (3-Methylbenzoyl)acetonitrile
Physico-chemical properties:
Melting point: 192° to 194° C.
Mass: 215 (M-HCl)$^+$

| Elementary analysis (as $C_{11}H_{14}N_5Cl \times 0.2C_2H_6O$) | | | | |
|---|---|---|---|---|
| | C (%) | H (%) | N (%) | Cl (%) |
| Theoretical | 52.47 | 6.00 | 26.37 | 13.35 |
| Measured | 51.99 | 5.95 | 26.29 | 13.07 |

Nuclear magnetic resonance spectrum (DMSO-$d_6$, TMS internal standard): δ: 2.37 (3H, s), 6.08 (1H, s), 7.24 (1H, d, J=7.3 Hz), 7.33–7.36 (1H, m), 7.66 (1H, d, J=7.8 Hz) 7.71 (1H, s), 9.18 (4H, br)

Example 63

End product: 5-Amino-3-propyl-1H-pyrazole-1-carboxamidine hydrochloride
Starting compound: Butanoylacetonitrile
Physico-chemical properties:
Melting point: 166° to 167° C.
Mass: 167 (M-HCl)$^+$ Nuclear magnetic resonance spectrum (DMSO-$d_6$, TMS internal) δ: 0.91 (3H, t, J=7.3 Hz), 1.54–1.63 (2H, m), 2.43 (2H, t, J=7.5 Hz), 5.54 (1H, s), 6.15 (2H, brs), 8.98 (4H, brs)

Example 64

0.1 g of 10% palladium-carbon were added to a solution of 0.6 g of 5-amino-3-(2-phenylethenyl)-1H-pyrazole-1-carboxamidine hydrochloride in 40 ml of methanol and stirred for 30 minutes in hydrogen atmosphere of normal pressure at room temperature. The reaction solution was filtered to remove the insoluble solids therefrom, and the solvent was removed by distillation under reduced pressure. The resulting residue was recrystallized from ethanol-ether to obtain 0.38 g of 5-amino-3-(2-phenylethyl)-1H-pyrazole-1-carboxamidine hydrochloride.

Physico-chemical properties:

Melting point: 187° to 189° C.

Mass: 229 (M-HCl)$^+$

| Elementary analysis (as $C_{12}H_{16}N_5Cl \times 0.2\,H_2O$) | | | | |
|---|---|---|---|---|
| | C (%) | H (%) | N (%) | Cl (%) |
| Theoretical | 53.51 | 6.14 | 26.00 | 13.16 |
| Measured | 53.36 | 6.07 | 25.95 | 13.43 |

Nuclear magnetic resonance spectrum (DMSO-$d_6$, TMS internal standard): δ: 2.64–3.04 (4H, m), 5.55 (1H, s), 7.09–7.39 (5H, m), 8.88 (4H, br)

Example 65

A catalytic amount of 10% palladium-carbon was added to a solution of 0.24 g of 5-amino-3-(4-nitrophenyl)-1H-pyrazole-1-carboxamidine hydrochloride in 40 ml of methanol and stirred for 30 minutes in a hydrogen atmosphere of normal pressure at room temperature. The reaction solution was filtered to remove the insoluble solids therefrom, and 0.5 ml of 4N hydrochloric acid-dioxane were added thereto. The solvents were removed by distillation under reduced pressure, and the resulting residue was recrystallized from ethanol-ether to obtain 0.16 g of 5-amino-3- (4-aminophenyl)-1H-pyrazole-1-carboxamidine dihydrochloride.

Physico-chemical properties:

Melting point: 219° to 222° C.

Mass: 217 (MH-2HCl)+

| Elementary analysis (as $C_{10}H_{14}N_6Cl_2 \times 0.2H_2O$) | | | | |
|---|---|---|---|---|
| | C (%) | H (%) | N (%) | Cl (%) |
| Theoretical | 41.03 | 4.96 | 28.71 | 24.22 |
| Measured | 41.10 | 4.91 | 28.64 | 24.42 |

Nuclear magnetic resonance spectrum (DMSO-$d_6$, TMS internal standard): δ: 6.06 (1H, s), 7.22 (2H, J=8.5 Hz), 7.85 (2H, d, J=8.5 Hz), 9.14 (4H, br)

TABLE 4

Formula for Examples 46–65

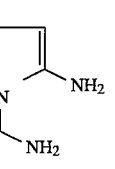

(Id)

| Example No. | $R^1$ | Salt |
|---|---|---|
| 46 | $(CH_3)_3C-$ | HCl |
| 47 | φ-CHCH— | HCl |
| 48 | 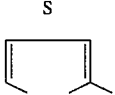 | HCl |
| 49 | 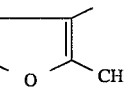 | HCl |
| 50 | 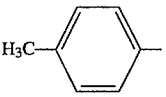 | HCl |
| 51 | 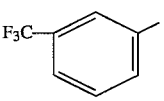 | HCl |
| 52 | 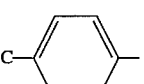 | HCl |
| 53 | 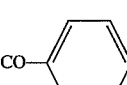 | HCl |
| 54 | 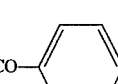 | HCl |
| 55 | 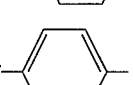 | HCl |
| 56 | 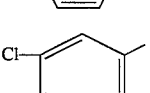 | HCl |
| 57 | 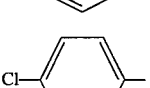 | HCl |
| 58 |  | HCl |

TABLE 4-continued

Formula for Examples 46–65 (Id)

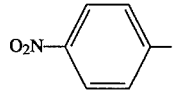

| Example No. | R¹ | Salt |
|---|---|---|
| 59 | 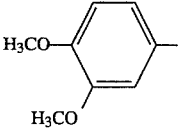 (O₂N-phenyl-) | HCl |
| 60 | (3,4-dimethoxyphenyl, H₃CO-, H₃CO-) | HCl |
| 61 | (3,4,5-trimethoxyphenyl, H₃CO-, H₃CO-, H₃CO-) | HCl |
| 62 | (m-tolyl, H₃C-) | HCl |
| 63 | CH₃CH₂CH₂— | HCl |
| 64 | φ-(CH₂)₂— | HCl |
| 65 | (H₂N-phenyl-) | 2HCl |

Example 66

A solution of 3.06 g of 1,1,1,5,5,5-hexafluoro-2,4-pentanedione in 10 ml of methanol was added little by little to a solution of 1.61 g of aminoguanidine hydrochloride in 5 ml of water, 40 ml of methanol and 1 ml of concentrated hydrochloric acid, and stirred overnight at room temperature.

The solvents were removed by distillation under reduced pressure, and the resulting residue was purified by silica gel chromatography(eluent: chloroform/methanol=5/1) and then recrystallized from ethanol-ether to obtain 2.66 g of 3,5-bis(trifluoromethyl)-5-hydroxy-2-pyrazoline-1-carboxamidine hydrochloride.

Physico-chemical properties:

Melting point: 182° to 187° C.

| Elementary analysis (as $C_6H_7N_4OF_6Cl$): | | | | | |
|---|---|---|---|---|---|
| | C (%) | H (%) | N (%) | F (%) | Cl (%) |
| Theoretical | 23.97 | 2.35 | 18.64 | 37.92 | 11.79 |
| Measured | 23.86 | 2.35 | 18.88 | 38.28 | 11.99 |

Nuclear magnetic resonance spectrum (DMSO-$d_6$.TMS internal standard): δ: 4.03 (2H,s), 8.37 (4H,brs), 10.63 (1H,brs)

Example 67

In the same manner as in Example 66, the following compound of Example 67 was obtained.

End product: 5-Hydroxy-3-methyl-5-trifluoromethyl-2-pyrazoline-1-carboximidamide hydrochloride Starting compound: 1,1,1-Trifluoro-2,4-pentanedione Physico-chemical properties:

Melting point: 190° to 196° C.

| Elementary analysis (as $C_6H_{10}N_4OF_3Cl.0.5H_2O$): | | |
|---|---|---|
| | C (%) | H (%) | N (%) |
| Theoretical | 28.29 | 4.34 | 21.92 |
| Measured | 27.94 | 3.96 | 21.77 |

Nuclear magnetic resonance spectrum (DMSO-$d_6$.TMS internal standard): δ: 2.07 (3H,s), 3.64 (2H, ABq, J=19.5 Hz), 7.94 (4H,br), 9.99 (1H,s)

Example 68

In the same manner as in Example 66, the following compound of Example 68 was obtained.

End product: 1,3a,4,5,6,6a-Hexahydro-6a-hydroxy-3-methyl-(1H)-cyclopentapyrazole-1-carboximidamide hydrochloride Starting compound: 2-Acetylcyclopentanone Physico-chemical properties:

Melting point: 155° to 158° C.

| Elementary analysis (as $C_8H_{15}N_4OCl$): | | | |
|---|---|---|---|
| | C (%) | H (%) | N (%) | Cl (%) |
| Theoretical | 43.94 | 6.91 | 25.62 | 16.21 |
| Measured | 43.65 | 6.96 | 25.66 | 16.14 |

Nuclear magnetic resonance spectrum (DMSO-$d_6$.TMS internal standard): δ: 1.28–1.42 (1H,M), 1.73–1.75 (2H, m), 2.01 (3H,s), 2.03–2.13 (2H, m), 2.22–2.26 (1H, m), 3.36–3.39 (1H,m), 7.40–7.90 (5H, m)

TABLE 5

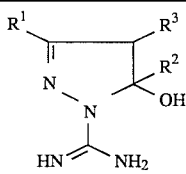

| Example No. | R¹ | R² | R³ | Salt |
|---|---|---|---|---|
| 66 | CF₃ | CF₃ | H | HCl |
| 67 | CH₃ | CF₃ | H | HCl |
| 68 | CH₃ | —CH₂—CH₂—CH₂— | | HCl |

What is claimed is:

1. A method of inhibiting the formation of advanced glycation endproducts which comprises administration of a compound of general formula (I):

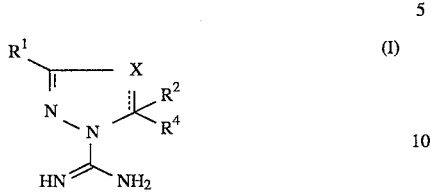

wherein $R^1$ represents a hydrogen atom, a lower alkyl group, or a phenyl group;

$R^2$ represents a hydrogen atom, a lower alkyl group, a phenyl group, an amino group, a lower alkoxy group, a carboxyl group, or a lower alkoxycarbonyl group; X represents a nitrogen atom, or a group of a formula —$CR^3$—; and $R^3$ represents a hydrogen atom, a lower alkyl group, a phenyl group, a halogen atom, or a lower alkanoyl group;

the dotted line represents an optional double bond when X is $CR^3$—

$R^4$ represents a hydroxy group when the optional double bond is not present;

with the proviso that when X represents $CR^3$— and $R^2$ represents hydrogen and the optional double bond is present, then $R^1$ together with $R^3$ can be a —CH=CH—CH=CH— group, optionally substituted by a hydrogen atom, a hydroxyl group, a nitro group, an amino group or a sulfamoyl group;

with the further proviso that when $R^1$ and $R^2$ both represent a lower alkyl group and X represents $CR^3$— and the dotted line represents a double bond then $R^3$ represents:

(i) a fluorine atom, a nitro group, an unsubstituted lower alkyl group having 3 or more carbon substituted by a lower alkanoyl group; or (ii) a lower alkyl group substituted by any of a halogen atom, a lower alkanoyl group, a lower alkoxy group, a lower alkoxycarbonyl group and a phenyl group of the formula:

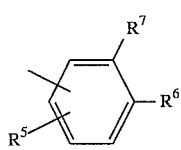

in which $R^5$ and $R^6$ and $R^7$ are the same or different and each represents a hydrogen atom, and amino group, a nitro group, a hydroxyl group, a lower alkyl group, a lower alkoxy group, a lower alkoxycarbonyl group or an aralkyloxy group, and $R^6$ and $R^7$ together may form a lower alkylenedioxy group; or (iii) a carbonyl group substituted by any of a hydroxyl group, a lower alkyl group, an aralkyloxy group, an optionally lower alkyl-substituted amino group and an optionally lower alkoxy substituted lower alkoxy group; or (iv) together with $R^2$ can form a lower alkylene group having 3 or more carbon atoms;

with the still further proviso that when X represents $CR^3$—, $R^3$ represents hydrogen, the double bond is present and $R^2$ represents an amino group, then $R^1$ can represent a lower alkyl-substituted or unsubstituted thienyl or furyl group, a phenyl-substituted lower alkyl or lower alkenyl group, or a phenyl group of the formula

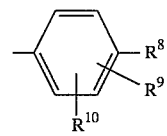

in which $R^8$, $R^9$ and $R^{10}$ are the same or different and each represents a hydrogen atom, a halogen atom, an amino group, a nitro group, or an optionally halogen-substituted lower alkyl or lower alkoxy group;

and with the still further proviso that when X represents $CR^3$—, the optional bond is not present and $R^4$ is a hydroxy group, then $R^1$ and $R2$ are the same or different and each represents a halogen atom-substituted or unsubstituted lower alkyl group; $R^3$ represents a hydrogen atom; and $R^2$ and $R^3$ may together form a lower alkylene group;

and the pharmaceutically acceptable acid addition salts thereof.

2. A method according to claim 1 wherein the compound administered is of the general formula (Ia)

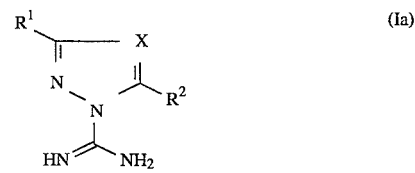

wherein $R^1$ represents a hydrogen atom, a lower alkyl group, or phenyl group;

$R^2$ represents a hydrogen atom, a lower alkyl group, a phenyl group, an amino group, a lower alkoxy group, a carboxyl group, or a lower alkoxycarbonyl group; X represents a nitrogen atom, or a group of a formula —$CR^3$=;

and $R^3$ represents a hydrogen atom, a lower alkyl group, a phenyl group, a halogen atom, or a lower alkanoyl group.

3. A method according to claim 2 wherein X is a $CR^3$— group.

4. The method according to claim 3 wherein the compound administered is 1-amidino-3,5-dimethylpyrazole hydrochloride or another pharmaceutically acceptable acid addition salt thereof.

5. A method according to claim 1 wherein the compound administered is a compound of the general formula (Ib)

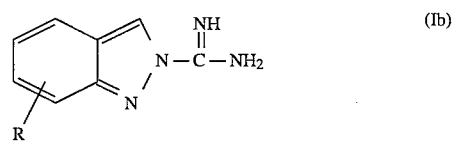

wherein R represents a hydrogen atom, a hydroxyl group, a nitro group, an amino group or a sulfamoyl group bonded to any carbon atom on the benzene ring of the indazole moiety;

and their pharmaceutically acceptable acid addition salts.

6. A method according to claim 5 wherein R is an amino group or a hydroxyl group.

7. The method according to claim 6 which is 7-amino-2H-indazole-2-carboxamidine dihydrochloride or another pharmaceutically acceptable acid addition salt thereof.

8. A method according to claim 1 wherein the compound administered is a compound of the general formula (Ic):

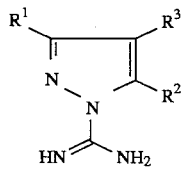

wherein $R^1$ represents a lower alkyl group;

$R^2$ represents a lower alkyl group;

$R^3$ represents
(i) a fluorine atom, a nitro group, an unsubstituted lower alkyl having 3 or more carbon atoms, or an amino group optionally substituted by a lower alkanoyl group or a lower alkoxycarbonyl group; or
(ii) a lower alkyl group substituted by any of a halogen atom, a lower alkanoyl group, a lower alkoxy group, a lower alkoxycarbonyl group and a phenyl group of a formula:

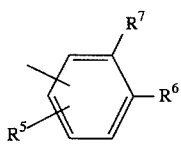

in which $R^5$ and $R^6$ and $R^7$ are same or different and each represents a hydrogen atom, an amino group, a nitro group, a hydroxyl group, a lower alkyl group, a lower alkoxy group, a lower alkoxycarbonyl group or an aralkyloxy group, and $R^6$ and $R^7$ may together form a lower alkylenedioxy group; or
(iii) a carbonyl group substituted by any of a hydroxyl group, a lower alkyl group, an aralkyloxy group, an optionally lower alkyl-substituted amino group and an optionally lower alkoxy-substituted lower alkoxy group; or
(iv) together with $R^2$ can form a lower alkylene group having 3 or more carbon atoms;

and their pharmaceutically acceptable acid addition salts, solvates and hydrates.

9. A method according to claim 8 wherein $R^1$ and $R^2$ are both methyl groups.

10. The method according to claim 9 which is 4-amino-3,5-dimethyl-1H-pyrazole-1-carboxamidine dihydrochloride or another pharmaceutically acceptable acid addition salt thereof.

11. A method according to claim 1 wherein the compound administered is a compound of the general formula

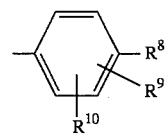

where $R^1$ represents a lower alkyl group having 3 or more carbon atoms, a lower alkyl-substituted or unsubstituted thienyl or furyl group, a phenyl-substituted lower alkyl or lower alkenyl group, or a phenyl group of a formula:

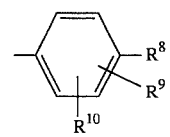

in which $R^8$, $R^9$ and $R^{10}$ are the same or different and each represents a hydrogen atom, a halogen atom, an amino group, a nitro group, or an optionally halogen-substituted lower alkyl or lower alkoxy group;

provided that when $R^8$ is a hydrogen atom or a bromine atom, one of $R^9$ and $R^{10}$ is a group except hydrogen.

12. A method according to claim 11 wherein $R^1$ is a phenyl group of the formula

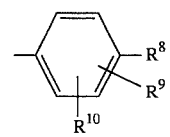

in which $R^8$, $R^9$ and $R^{10}$ are the same or different and each represents a hydrogen atom, a halogen atom, an amino group, a nitro group, or an optionally halogen-substituted lower alkyl or lower alkoxy group;

provided that when $R^8$ is a hydrogen atom or a bromine atom, one of $R^9$ and $R^{10}$ is a group except hydrogen.

13. The method according to claim 12 which is 5-amino-3-(4-aminophenyl)-1H-pyrazole dihydrochloride or another pharmaceutically acceptable acid addition salt thereof.

14. A method according to claim 1 wherein the compound administered is a compound of the general formula

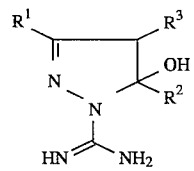

where $R^1$ and $R^2$ are same or different and each represents a halogen atom-substituted or unsubstituted lower alkyl group, provided that when one of them is methyl group, the other is a group except it;

$R^3$ represents a hydrogen atom; and $R^2$ and $R^3$ may together form a lower alkylene group.

15. A method according to claim 14 wherein $R^2$ is a trifluoromethyl group.

16. A method according to claim 15 which is 5-hydroxy-3-methyl-5-trifluoromethyl-2-pyrazoline-1 -carboximidamide hydrochloride or another pharmaceutically acceptable acid addition salt thereof.

17. A compound of the general formula (Ib)

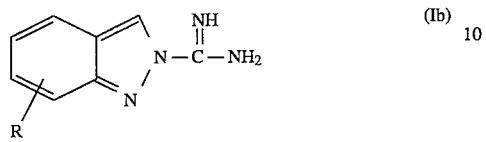

wherein R represents a hydrogen atom, a hydroxyl group, a nitro group, an amino group or a sulfamoyl group bonded to any carbon atom on the benzene ring of the indazole moiety; and their pharmaceutically acceptable acid addition salts.

18. A compound according to claim 17 wherein R is an amino group or a hydroxyl group.

19. The compound according to claim 18 which is 7-amino-2H-indazole-2-carboxamidine dihydrochloride or another pharmaceutically acceptable acid addition salt thereof.

20. A compound of the general formula (Ic):

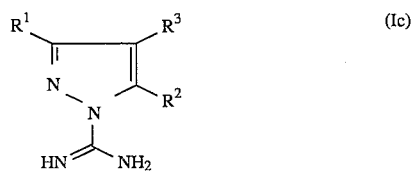

wherein $R^1$ represents a lower alkyl group;

$R^2$ represents a lower alkyl group;

$R^3$ represents
(i) a fluorine atom, a nitro group, an unsubstituted lower alkyl having 3 or more carbon atoms, or an amino group optionally substituted by a lower alkanoyl group or a lower alkoxycarbonyl group; or
(ii) a lower alkyl group substituted by any of a halogen atom, a lower alkanoyl group, a lower alkoxy group, a lower alkoxycarbonyl group and a phenyl group of a formula:

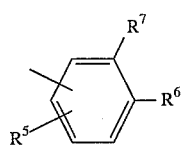

in which $R^5$, and $R^6$ and $R^7$ are same or different and each represents a hydrogen atom, an amino group, a nitro group, a hydroxyl group, a lower alkyl group, a lower alkoxy group, a lower alkoxycarbonyl group or an aralkyloxy group, and $R^6$ and $R^7$ may together form a lower alkylenedioxy group; or
(iii) a carbonyl group substituted by any of a hydroxyl group, a lower alkyl group, an aralkyloxy group, an optionally lower alkyl-substituted amino group and an optionally lower alkoxy-substituted lower alkoxy group; or
(iv) together with $R^2$ can form a lower alkylene group having 3 or more carbon atoms;

and their pharmaceutically acceptable acid addition salts, solvates and hydrates.

21. A compound according to claim 20 wherein $R^1$ and $R^2$ are both methyl groups.

22. The compound according to claim 21 which is 4-amino-3,5-dimethyl-1H-pyrazole-1-carboxamidine dihydrochloride or another pharmaceutically acceptable acid addition salt thereof.

23. A compound of the general formula

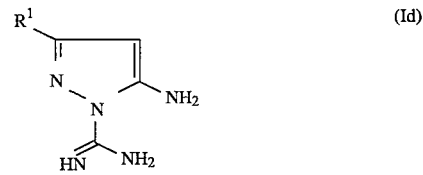

where $R^1$ represents a lower alkyl group having 3 or more carbon atoms, a lower alkyl-substituted or unsubstituted thienyl or furyl group, a phenyl-substituted lower alkyl or lower alkenyl group, or a phenyl group of a formula:

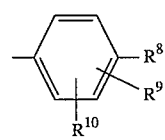

in which $R^8$, $R^9$ and $R^{10}$ are the same or different and each represents a hydrogen atom, a halogen atom, an amino group, a nitro group, or an optionally halogen-substituted lower alkyl or lower alkoxy group;

provided that when $R^8$ is a hydrogen atom or a bromine atom, one of $R^9$ and $R^{10}$ is a group except hydrogen.

24. A compound according to claim 23 wherein $R^1$ is a phenyl group of the formula

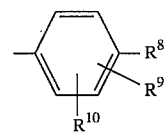

in which $R^8$, $R^9$ and $R^{10}$ are the same or different and each represents a hydrogen atom, a halogen atom, an amino group, a nitro group, or an optionally halogen-substituted lower alkyl or lower alkoxy group;

provided that when $R^8$ is a hydrogen atom or a bromine atom, one of $R^9$ and $R^{10}$ is a group except hydrogen.

25. The compound according to claim 24 which is 5-amino-3-(4-aminophenyl)-1H-pyrazole dihydrochloride or another pharmaceutically acceptable acid addition salt thereof.

26. A compound of the general formula

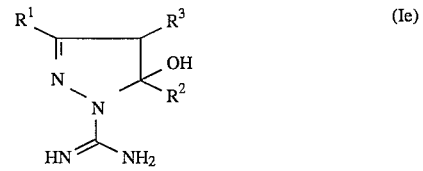

where $R^1$ and $R^2$ are same or different and each represents a halogen atom-substituted or unsubstituted lower alkyl group, provided that when one of them is methyl group, the other is a group except it;

$R^3$ represents a hydrogen atom; and $R^2$ and $R^3$ may together form a lower alkylene group.

27. A compound according to claim 26 wherein $R^2$ is a trifluoromethyl group.

28. A compound according to claim 27 which is 5-hydroxy-3-methyl-5-trifluoromethyl-2-pyrazoline-1-carboxyimidamide hydrochloride or another pharmaceutically acceptable acid addition salt thereof.

29. The method according to claim 3 wherein the compound is 1-amidinopyrazole hydrochloride or another pharmaceutically acceptable acid addition salt thereof.

30. The method according to claim 3 wherein the compound is 1-amidino-4-chloro-3,5-dimethylpyrazole nitrate or another pharmaceutically acceptable acid addition salt thereof.

31. The method according to claim 3 wherein the compound is 1-amidino-4-bromo-3,5-dimethylpyrazole nitrate or another pharmaceutically acceptable acid addition salt thereof.

32. The method according to claim 3 wherein the compound is 1-amidino-5-aminopyrazole hydrochloride or another pharmaceutically acceptable acid addition salt thereof.

33. The method according to claim 3 wherein the compound is 1-amidino-5-amino-3-methylpyrazole hydrochloride or another pharmaceutically acceptable acid addition salt thereof.

34. The method according to claim 3 wherein the compound is 1-amidino-5-amino-3-phenylpyrazole hydrochloride or another pharmaceutically acceptable acid addition salt thereof.

35. The method according to claim 3 wherein the compound is ethyl (1-amidino-3-methylpyrazol-5-yl)carboxylate hydrochloride or another pharmaceutically acceptable acid addition salt thereof.

36. The method according to claim 3 wherein the compound is 4-acetyl-1-amidino-5-methylpyrazole hydrochloride or another pharmaceutically acceptable acid addition salt thereof.

* * * * *